United States Patent
Strickland

(10) Patent No.: US 11,111,477 B2
(45) Date of Patent: Sep. 7, 2021

(54) LIVE CELL CONSTRUCTS FOR PRODUCTION OF CULTURED MILK PRODUCT AND METHODS USING THE SAME

(71) Applicant: BIOMILQ, Inc., Durham, NC (US)

(72) Inventor: Leila Strickland, Hillsborough, NC (US)

(73) Assignee: BIOMILQ, Inc., Durham, NC (US)

( * ) Notice: Subject to any disclaimer, the term of this patent is extended or adjusted under 35 U.S.C. 154(b) by 0 days.

(21) Appl. No.: 17/247,672

(22) Filed: Dec. 18, 2020

(65) Prior Publication Data

US 2021/0207090 A1 Jul. 8, 2021

Related U.S. Application Data

(60) Provisional application No. 63/199,164, filed on Dec. 10, 2020, provisional application No. 62/958,407, filed on Jan. 8, 2020.

(51) Int. Cl.
*C12N 5/071* (2010.01)
*A23C 9/12* (2006.01)

(52) U.S. Cl.
CPC .............. *C12N 5/0631* (2013.01); *A23C 9/12* (2013.01); *C12N 2500/02* (2013.01); *C12N 2513/00* (2013.01); *C12N 2523/00* (2013.01); *C12N 2533/90* (2013.01)

(58) Field of Classification Search
CPC .............. C12N 5/0631; C12N 2500/02; C12N 2533/90; C12N 2523/00; C12N 2513/00
See application file for complete search history.

(56) References Cited

U.S. PATENT DOCUMENTS

| | | | |
|---|---|---|---|
| 6,358,920 B1 | 3/2002 | Blaschuk et al. | |
| 2013/0344490 A1 | 12/2013 | Kim | |
| 2015/0079584 A1 | 3/2015 | Gevaert et al. | |
| 2017/0267970 A1* | 9/2017 | Gupta | C12N 5/0068 |
| 2018/0066220 A1* | 3/2018 | Nath | C12M 25/10 |
| 2019/0211296 A1 | 7/2019 | Allbritton | |

FOREIGN PATENT DOCUMENTS

| | | |
|---|---|---|
| EP | 0911389 A2 | 4/1999 |
| EP | 0911389 A2 | 4/1999 |
| WO | WO-20210142241 A1 | 7/2021 |

OTHER PUBLICATIONS

Cho et al. Construction of a 3D mammary duct based on spatial localization of the extracellular matrix. NPG Asia Materials (2018) 10: 970-981; supplementary information attached (p. 1-10) (Year: 2018).*

Yonemura. Differential Sensitivity of Epithelial Cells to Extracellular Matrix in Polarity Establishment. PLoS One 9(11): e112922. p. 1-10 (Year: 2014).*

Arèvalo Turrubiarte, M., et al., Phenotypic and functional characterization of two bovine mammary epithelial cell lines in 2D and 3D models, Am J Physiol, 310: C348-C356, (2016).

Blatchford D.R., et al., Milk Secretion in Cultured Mammary Epithelial Cells, In: Kitagawa, Y., et al. (eds), Animal Cell Technology: Basic & Applied Aspects, Springer, Dordrecht, 10: 141-145 (1999).

Chen, G., et al., Isolation, culture, and differentiation of mammary epithelial stem/progenitor cells from fresh or ex vivo cultured human breast tissue, Curr Protoc Cell Biol, 82(1): e65 (2019).

Morada, M., et al., Continuous culture of Cryptosporidium parvum using hollow fiber technology, Int J for Parasitol, 46(1): 21-29 (2016).

Sharfstein, S.T., et al., Functional Differentiation and Primary Metabolism of Mouse Mammary Epithelial Cells in Extended-Batch and Hollow-Fiber Culture, Biotechnol and Bioeng, 40(6): 672-680 (1992).

Gourdou, I., et al., Development of a constitutively active mutant form of the prolactin receptor, a member of the cytokine receptor family, Mol Endo, 10(1): 45-56 (1996).

Shennan, D.B., et al., Transport of milk constituents by the mammary gland, Physiol Rev, 80(3): 925-951 (2000).

U.S. Appl. No. 17/301,216 Office Action dated Jul. 12, 2021.

Watson, D.L., Immunological functions of the mammary gland and its secretion—Comparative review, Aust J Biol Sci, 33(4): 403-422 (1980).

Yang, N.S., et al., Growth of human mammary epithelial cells on collagen gel surfaces, Cancer Res, 41 (10): 4093-4100 (1983).

Co-Pending U.S. Appl. No. 17/301,216, filed Mar. 29, 2021.

Gourdou, I., et al.. Expression by transgenesis of a constitutively active mutant form of the prolactin receptor induces premature abnormal development of the mouse mammary gland and lactation failure, Biol Reprod, 70(3): 718-728 (2004).

Kozlowski, M., et al., Differences in growth and transcriptomic profile of bovine mammary epithelial monolayer and three-dimensional cell cultures, J Physiol Pharmacol, 60(Suppl 1): 5-14 (2009).

O'Brien, L.E., et al., Rac1 orientates epithelial apical polarity through effects on basolateral laminin assembly, Nat Cell Biol, 3(9): 831-838 (2001).

PCT/US2020/066209 Insternational Search Report and Written Opinion dated Apr. 22, 2021.

* cited by examiner

*Primary Examiner* — Taeyoon Kim

(74) *Attorney, Agent, or Firm* — Goodwin Procter LLP

(57) ABSTRACT

This invention relates to live cell constructs for in vitro and/or ex vivo production of cultured milk products from mammary cells, methods of producing isolated cultured milk products from mammary cells, bioreactors for producing isolated cultured milk products, and cultured milk products.

7 Claims, 6 Drawing Sheets

Specification includes a Sequence Listing.

```
                        SEQUENCE LISTING

<160> NUMBER OF SEQ ID NOS: 4

<210> SEQ ID NO 1
<211> LENGTH: 622
<212> TYPE: PRT
<213> ORGANISM: Homo sapiens

<400> SEQUENCE: 1

Met Lys Glu Asn Val Ala Ser Ala Thr Val Phe Thr Leu Leu Leu Phe
1               5                   10                  15

Leu Asn Thr Cys Leu Leu Asn Gly Gln Leu Pro Pro Gly Lys Pro Glu
            20                  25                  30

Ile Phe Lys Cys Arg Ser Pro Asn Lys Glu Thr Phe Thr Cys Trp Trp
        35                  40                  45

Arg Pro Gly Thr Asp Gly Gly Leu Pro Thr Asn Tyr Ser Leu Thr Tyr
    50                  55                  60

His Arg Glu Gly Glu Thr Leu Met His Glu Cys Pro Asp Tyr Ile Thr
65                  70                  75                  80

Gly Gly Pro Asn Ser Cys His Phe Gly Lys Gln Tyr Thr Ser Met Trp
                85                  90                  95

Arg Thr Tyr Ile Met Met Val Asn Ala Thr Asn Gln Met Gly Ser Ser
```

```
                    100                 105                     110
Phe Ser Asp Glu Leu Tyr Val Asp Val Thr Tyr Ile Val Gln Pro Asp
            115                 120                 125
Pro Pro Leu Glu Leu Ala Val Glu Val Lys Gln Pro Glu Asp Arg Lys
    130                 135                 140
Pro Tyr Leu Trp Ile Lys Trp Ser Pro Pro Thr Leu Ile Asp Leu Lys
145                 150                 155                 160
Thr Gly Trp Phe Thr Leu Leu Tyr Glu Ile Arg Leu Lys Pro Glu Lys
                165                 170                 175
Ala Ala Glu Trp Glu Ile His Phe Ala Gly Gln Gln Thr Glu Phe Lys
            180                 185                 190
Ile Leu Ser Leu His Pro Gly Gln Lys Tyr Leu Val Gln Val Arg Cys
        195                 200                 205
Lys Pro Asp His Gly Tyr Trp Ser Ala Trp Ser Pro Ala Thr Phe Ile
    210                 215                 220
Gln Ile Pro Ser Asp Phe Thr Met Asn Asp Thr Thr Val Trp Ile Ser
225                 230                 235                 240
Val Ala Val Leu Ser Ala Val Ile Cys Leu Ile Ile Val Trp Ala Val
                245                 250                 255
Ala Leu Lys Gly Tyr Ser Met Val Thr Cys Ile Phe Pro Pro Val Pro
            260                 265                 270
Gly Pro Lys Ile Lys Gly Phe Asp Ala His Leu Leu Glu Lys Gly Lys
        275                 280                 285
Ser Glu Glu Leu Leu Ser Ala Leu Gly Cys Gln Asp Phe Pro Pro Thr
    290                 295                 300
Ser Asp Tyr Glu Asp Leu Leu Val Glu Tyr Leu Glu Val Asp Asp Ser
305                 310                 315                 320
Glu Asp Gln His Leu Met Ser Val His Ser Lys Glu His Pro Ser Gln
                325                 330                 335
Gly Met Lys Pro Thr Tyr Leu Asp Pro Asp Thr Asp Ser Gly Arg Gly
            340                 345                 350
Ser Cys Asp Ser Pro Ser Leu Leu Ser Glu Lys Cys Glu Glu Pro Gln
        355                 360                 365
Ala Asn Pro Ser Thr Phe Tyr Asp Pro Glu Val Ile Glu Lys Pro Glu
    370                 375                 380
Asn Pro Glu Thr Thr His Thr Trp Asp Pro Gln Cys Ile Ser Met Glu
385                 390                 395                 400
Gly Lys Ile Pro Tyr Phe His Ala Gly Gly Ser Lys Cys Ser Thr Trp
                405                 410                 415
Pro Leu Pro Gln Pro Ser Gln His Asn Pro Arg Ser Ser Tyr His Asn
            420                 425                 430
Ile Thr Asp Val Cys Glu Leu Ala Val Gly Pro Ala Gly Ala Pro Ala
        435                 440                 445
Thr Leu Leu Asn Glu Ala Gly Lys Asp Ala Leu Lys Ser Ser Gln Thr
    450                 455                 460
Ile Lys Ser Arg Glu Glu Gly Lys Ala Thr Gln Gln Arg Glu Val Glu
465                 470                 475                 480
Ser Phe His Ser Glu Thr Asp Gln Asp Thr Pro Trp Leu Leu Pro Gln
                485                 490                 495
Glu Lys Thr Pro Phe Gly Ser Ala Lys Pro Leu Asp Tyr Val Glu Ile
            500                 505                 510
His Lys Val Asn Lys Asp Gly Ala Leu Ser Leu Leu Pro Lys Gln Arg
        515                 520                 525
```

```
Glu Asn Ser Gly Lys Pro Lys Pro Gly Thr Pro Glu Asn Asn Lys
        530                 535                 540

Glu Tyr Ala Lys Val Ser Gly Val Met Asp Asn Asn Ile Leu Val Leu
545                 550                 555                 560

Val Pro Asp Pro His Ala Lys Asn Val Ala Cys Phe Glu Glu Ser Ala
                565                 570                 575

Lys Glu Ala Pro Pro Ser Leu Glu Gln Asn Gln Ala Glu Lys Ala Leu
            580                 585                 590

Ala Asn Phe Thr Ala Thr Ser Ser Lys Cys Arg Leu Gln Leu Gly Gly
        595                 600                 605

Leu Asp Tyr Leu Asp Pro Ala Cys Phe Thr His Ser Phe His
    610                 615                 620

<210> SEQ ID NO 2
<211> LENGTH: 1205
<212> TYPE: PRT
<213> ORGANISM: Homo sapiens

<400> SEQUENCE: 2

Met Asn Gly Tyr Ala Glu Phe Pro Pro Ser Pro Ser Asn Pro Thr Lys
1               5                   10                  15

Glu Pro Val Glu Pro Gln Pro Ser Gln Val Pro Leu Gln Glu Asp Val
                20                  25                  30

Asp Met Ser Ser Gly Ser Ser His Glu Thr Asn Glu Asn Cys Ser
            35                  40                  45

Thr Gly Arg Asp Ser Gln Gly Ser Asp Cys Asp Asp Ser Gly Lys Glu
        50                  55                  60

Leu Gly Met Leu Val Glu Pro Pro Asp Ala Arg Gln Ser Pro Asp Thr
65                  70                  75                  80

Phe Ser Leu Met Met Ala Lys Ser Glu His Asn Pro Ser Thr Ser Gly
                85                  90                  95

Cys Ser Ser Asp Gln Ser Ser Lys Val Asp Thr His Lys Glu Leu Ile
            100                 105                 110

Lys Thr Leu Lys Glu Leu Lys Val His Leu Pro Ala Asp Lys Lys Ala
        115                 120                 125

Lys Gly Lys Ala Ser Thr Leu Ala Thr Leu Lys Tyr Ala Leu Arg Ser
    130                 135                 140

Val Lys Gln Val Lys Ala Asn Glu Glu Tyr Tyr Gln Leu Leu Met Ser
145                 150                 155                 160

Ser Glu Gly His Pro Cys Gly Ala Asp Val Pro Ser Tyr Thr Val Glu
                165                 170                 175

Glu Met Glu Ser Val Thr Ser Glu His Ile Val Lys Asn Ala Asp Met
            180                 185                 190

Phe Ala Val Ala Val Ser Leu Val Ser Gly Lys Ile Leu Tyr Ile Ser
        195                 200                 205

Asp Gln Val Ala Ser Ile Phe His Cys Lys Arg Asp Ala Phe Ser Asp
    210                 215                 220

Ala Lys Phe Val Glu Phe Leu Ala Pro His Asp Val Gly Val Phe His
225                 230                 235                 240

Ser Phe Thr Ser Pro Tyr Lys Leu Pro Leu Trp Ser Met Cys Ser Gly
                245                 250                 255

Ala Asp Ser Phe Thr Gln Glu Cys Met Glu Glu Lys Ser Phe Phe Cys
            260                 265                 270

Arg Val Ser Val Arg Lys Ser His Glu Asn Glu Ile Arg Tyr His Pro
```

```
                275                 280                 285
Phe Arg Met Thr Pro Tyr Leu Val Lys Val Arg Asp Gln Gln Gly Ala
290                 295                 300
Glu Ser Gln Leu Cys Cys Leu Leu Ala Glu Arg Val His Ser Gly
305                 310                 315                 320
Tyr Glu Ala Pro Arg Ile Pro Pro Glu Lys Arg Ile Phe Thr Thr Thr
                325                 330                 335
His Thr Pro Asn Cys Leu Phe Gln Asp Val Asp Glu Arg Ala Val Pro
                340                 345                 350
Leu Leu Gly Tyr Leu Pro Gln Asp Leu Ile Glu Thr Pro Val Leu Val
                355                 360                 365
Gln Leu His Pro Ser Asp Arg Pro Leu Met Leu Ala Ile His Lys Lys
370                 375                 380
Ile Leu Gln Ser Gly Gly Gln Pro Phe Asp Tyr Ser Pro Ile Arg Phe
385                 390                 395                 400
Arg Ala Arg Asn Gly Glu Tyr Ile Thr Leu Asp Thr Ser Trp Ser Ser
                405                 410                 415
Phe Ile Asn Pro Trp Ser Arg Lys Ile Ser Phe Ile Ile Gly Arg His
                420                 425                 430
Lys Val Arg Val Gly Pro Leu Asn Glu Asp Val Phe Ala Ala His Pro
                435                 440                 445
Cys Thr Glu Glu Lys Ala Leu His Pro Ser Ile Gln Glu Leu Thr Glu
450                 455                 460
Gln Ile His Arg Leu Leu Leu Gln Pro Val Pro His Ser Gly Ser Ser
465                 470                 475                 480
Gly Tyr Gly Ser Leu Gly Ser Asn Gly Ser His Glu His Leu Met Ser
                485                 490                 495
Gln Thr Ser Ser Ser Asp Ser Asn Gly His Glu Asp Ser Arg Arg Arg
                500                 505                 510
Arg Ala Glu Ile Cys Lys Asn Gly Asn Lys Thr Lys Asn Arg Ser His
                515                 520                 525
Tyr Ser His Glu Ser Gly Glu Gln Lys Lys Ser Val Thr Glu Met
                530                 535                 540
Gln Thr Asn Pro Pro Ala Glu Lys Lys Ala Val Pro Ala Met Glu Lys
545                 550                 555                 560
Asp Ser Leu Gly Val Ser Phe Pro Glu Glu Leu Ala Cys Lys Asn Gln
                565                 570                 575
Pro Thr Cys Ser Tyr Gln Gln Ile Ser Cys Leu Asp Ser Val Ile Arg
                580                 585                 590
Tyr Leu Glu Ser Cys Asn Glu Ala Ala Thr Leu Lys Arg Lys Cys Glu
                595                 600                 605
Phe Pro Ala Asn Val Pro Ala Leu Arg Ser Ser Asp Lys Arg Lys Ala
                610                 615                 620
Thr Val Ser Pro Gly Pro His Ala Gly Glu Ala Glu Pro Pro Ser Arg
625                 630                 635                 640
Val Asn Ser Arg Thr Gly Val Gly Thr His Leu Thr Ser Leu Ala Leu
                645                 650                 655
Pro Gly Lys Ala Glu Ser Val Ala Ser Leu Thr Ser Gln Cys Ser Tyr
                660                 665                 670
Ser Ser Thr Ile Val His Val Gly Asp Lys Lys Pro Gln Pro Glu Leu
                675                 680                 685
Glu Met Val Glu Asp Ala Ala Ser Gly Pro Glu Ser Leu Asp Cys Leu
690                 695                 700
```

```
Ala Gly Pro Ala Leu Ala Cys Gly Leu Ser Gln Glu Lys Glu Pro Phe
705                 710                 715                 720

Lys Lys Leu Gly Leu Thr Lys Glu Val Leu Ala Ala His Thr Gln Lys
            725                 730                 735

Glu Glu Gln Ser Phe Leu Gln Lys Phe Lys Glu Ile Arg Lys Leu Ser
        740                 745                 750

Ile Phe Gln Ser His Cys His Tyr Tyr Leu Gln Glu Arg Ser Lys Gly
    755                 760                 765

Gln Pro Ser Glu Arg Thr Ala Pro Gly Leu Arg Asn Thr Ser Gly Ile
770                 775                 780

Asp Ser Pro Trp Lys Lys Thr Gly Lys Asn Arg Lys Leu Lys Ser Lys
785                 790                 795                 800

Arg Val Lys Pro Arg Asp Ser Ser Glu Ser Thr Gly Ser Gly Gly Pro
                805                 810                 815

Val Ser Ala Arg Pro Pro Leu Val Gly Leu Asn Ala Thr Ala Trp Ser
            820                 825                 830

Pro Ser Asp Thr Ser Gln Ser Ser Cys Pro Ala Val Pro Phe Pro Ala
        835                 840                 845

Pro Val Pro Ala Ala Tyr Ser Leu Pro Val Phe Pro Ala Pro Gly Thr
    850                 855                 860

Val Ala Ala Pro Pro Ala Pro Pro His Ala Ser Phe Thr Val Pro Ala
865                 870                 875                 880

Val Pro Val Asp Leu Gln His Gln Phe Ala Val Gln Pro Pro Pro Phe
                885                 890                 895

Pro Ala Pro Leu Ala Pro Val Met Ala Phe Met Leu Pro Ser Tyr Ser
            900                 905                 910

Phe Pro Ser Gly Thr Pro Asn Leu Pro Gln Ala Phe Phe Pro Ser Gln
        915                 920                 925

Pro Gln Phe Pro Ser His Pro Thr Leu Thr Ser Glu Met Ala Ser Ala
    930                 935                 940

Ser Gln Pro Glu Phe Pro Glu Gly Gly Thr Gly Ala Met Gly Thr Thr
945                 950                 955                 960

Gly Ala Thr Glu Thr Ala Ala Val Gly Ala Asp Cys Lys Pro Gly Thr
                965                 970                 975

Ser Arg Asp Gln Gln Pro Lys Ala Pro Leu Thr Arg Asp Glu Pro Ser
            980                 985                 990

Asp Thr Gln Asn Ser Asp Ala Leu Ser Thr Ser Ser Gly Leu Leu Asn
        995                 1000                1005

Leu Leu Leu Asn Glu Asp Leu Cys Ser Ala Ser Gly Ser Ala Ala
        1010                1015                1020

Ser Glu Ser Leu Gly Ser Gly Ser Leu Gly Cys Asp Ala Ser Pro
        1025                1030                1035

Ser Gly Ala Gly Ser Ser Asp Thr Ser His Thr Ser Lys Tyr Phe
        1040                1045                1050

Gly Ser Ile Asp Ser Ser Glu Asn Asn His Lys Ala Lys Met Asn
        1055                1060                1065

Thr Gly Met Glu Glu Ser Glu His Phe Ile Lys Cys Val Leu Gln
        1070                1075                1080

Asp Pro Ile Trp Leu Leu Met Ala Asp Ala Asp Ser Ser Val Met
        1085                1090                1095

Met Thr Tyr Gln Leu Pro Ser Arg Asn Leu Glu Ala Val Leu Lys
        1100                1105                1110
```

-continued

Glu Asp Arg Glu Lys Leu Lys Leu Leu Gln Lys Leu Gln Pro Arg
1115                1120                1125

Phe Thr Glu Ser Gln Lys Gln Glu Leu Arg Glu Val His Gln Trp
    1130                1135                1140

Met Gln Thr Gly Gly Leu Pro Ala Ala Ile Asp Val Ala Glu Cys
1145                1150                1155

Val Tyr Cys Glu Asn Lys Glu Lys Gly Asn Ile Cys Ile Pro Tyr
    1160                1165                1170

Glu Glu Asp Ile Pro Ser Leu Gly Leu Ser Glu Val Ser Asp Thr
1175                1180                1185

Lys Glu Asp Glu Asn Gly Ser Pro Leu Asn His Arg Ile Glu Glu
    1190                1195                1200

Gln Thr
1205

<210> SEQ ID NO 3
<211> LENGTH: 376
<212> TYPE: PRT
<213> ORGANISM: Homo sapiens

<400> SEQUENCE: 3

Met Lys Glu Asn Val Ala Ser Ala Thr Val Phe Thr Leu Leu Leu Phe
1               5                   10                  15

Leu Asn Thr Cys Leu Leu Asn Gly Gln Leu Pro Pro Gly Lys Pro Glu
            20                  25                  30

Ile Phe Lys Cys Arg Ser Pro Asn Lys Glu Thr Phe Thr Cys Trp Trp
        35                  40                  45

Arg Pro Gly Thr Asp Gly Gly Leu Pro Thr Asn Tyr Ser Leu Thr Tyr
    50                  55                  60

His Arg Glu Gly Glu Thr Leu Met His Glu Cys Pro Asp Tyr Ile Thr
65                  70                  75                  80

Gly Gly Pro Asn Ser Cys His Phe Gly Lys Gln Tyr Thr Ser Met Trp
                85                  90                  95

Arg Thr Tyr Ile Met Met Val Asn Ala Thr Asn Gln Met Gly Ser Ser
            100                 105                 110

Phe Ser Asp Glu Leu Tyr Val Asp Val Thr Tyr Ile Val Gln Pro Asp
        115                 120                 125

Pro Pro Leu Glu Leu Ala Val Glu Val Lys Gln Pro Glu Asp Arg Lys
    130                 135                 140

Pro Tyr Leu Trp Ile Lys Trp Ser Pro Pro Thr Leu Ile Asp Leu Lys
145                 150                 155                 160

Thr Gly Trp Phe Thr Leu Leu Tyr Glu Ile Arg Leu Lys Pro Glu Lys
                165                 170                 175

Ala Ala Glu Trp Glu Ile His Phe Ala Gly Gln Gln Thr Glu Phe Lys
            180                 185                 190

Ile Leu Ser Leu His Pro Gly Gln Lys Tyr Leu Val Gln Val Arg Cys
        195                 200                 205

Lys Pro Asp His Gly Tyr Trp Ser Ala Trp Ser Pro Ala Thr Phe Ile
    210                 215                 220

Gln Ile Pro Ser Asp Phe Thr Met Asn Asp Thr Thr Val Trp Ile Ser
225                 230                 235                 240

Val Ala Val Leu Ser Ala Val Ile Cys Leu Ile Ile Val Trp Ala Val
                245                 250                 255

Ala Leu Lys Gly Tyr Ser Met Val Thr Cys Ile Phe Pro Pro Val Pro
            260                 265                 270

```
Gly Pro Lys Ile Lys Gly Phe Asp Ala His Leu Leu Glu Lys Gly Lys
            275                 280                 285

Ser Glu Glu Leu Leu Ser Ala Leu Gly Cys Gln Asp Phe Pro Pro Thr
        290                 295                 300

Ser Asp Tyr Glu Asp Leu Leu Val Glu Tyr Leu Glu Val Asp Asp Ser
305                 310                 315                 320

Glu Asp Gln His Leu Met Ser Val His Ser Lys Glu His Pro Ser Gln
                325                 330                 335

Gly Asp Pro Leu Met Leu Gly Ala Ser His Tyr Lys Asn Leu Lys Ser
            340                 345                 350

Tyr Arg Pro Arg Lys Ile Ser Ser Gln Gly Arg Leu Ala Val Phe Thr
        355                 360                 365

Lys Ala Thr Leu Thr Thr Val Gln
    370                 375

<210> SEQ ID NO 4
<211> LENGTH: 1163
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Ala Gly Trp Ile Gln Ala Gln Gln Leu Gln Gly Asp Ala Leu Arg
1               5                   10                  15

Gln Met Gln Val Leu Tyr Gly Gln His Phe Pro Ile Glu Val Arg His
            20                  25                  30

Tyr Leu Ala Gln Trp Ile Glu Ser Gln Pro Trp Asp Ala Ile Asp Leu
        35                  40                  45

Asp Asn Pro Gln Asp Arg Ala Gln Ala Thr Gln Leu Leu Glu Gly Leu
    50                  55                  60

Val Gln Glu Leu Gln Lys Lys Ala Glu His Gln Val Gly Glu Asp Gly
65                  70                  75                  80

Phe Leu Leu Lys Ile Lys Leu Gly His Tyr Ala Thr Gln Leu Gln Lys
                85                  90                  95

Thr Tyr Asp Arg Cys Pro Leu Glu Leu Val Arg Cys Ile Arg His Ile
            100                 105                 110

Leu Tyr Asn Glu Gln Arg Leu Val Arg Glu Ala Asn Asn Cys Ser Ser
        115                 120                 125

Pro Ala Gly Ile Leu Val Asp Ala Met Ser Gln Lys His Leu Gln Ile
    130                 135                 140

Asn Gln Thr Phe Glu Glu Leu Arg Leu Val Thr Gln Asp Thr Glu Asn
145                 150                 155                 160

Glu Leu Lys Lys Leu Gln Gln Thr Gln Glu Tyr Phe Ile Ile Gln Tyr
                165                 170                 175

Gln Glu Ser Leu Arg Ile Gln Ala Gln Phe Ala Gln Leu Ala Gln Leu
            180                 185                 190

Ser Pro Gln Glu Arg Leu Ser Arg Glu Thr Ala Leu Gln Gln Lys Gln
        195                 200                 205

Val Ser Leu Glu Ala Trp Leu Gln Arg Glu Ala Gln Thr Leu Gln Gln
    210                 215                 220

Tyr Arg Val Glu Leu Ala Glu Lys His Gln Lys Thr Leu Gln Leu Leu
225                 230                 235                 240

Arg Lys Gln Gln Thr Ile Ile Leu Asp Asp Glu Leu Ile Gln Trp Lys
```

```
                245                 250                 255
Arg Arg Gln Gln Leu Ala Gly Asn Gly Gly Pro Pro Glu Gly Ser Leu
            260                 265                 270

Asp Val Leu Gln Ser Trp Cys Glu Lys Leu Ala Glu Ile Ile Trp Gln
            275                 280                 285

Asn Arg Gln Gln Ile Arg Arg Ala Glu His Leu Cys Gln Gln Leu Pro
290                 295                 300

Ile Pro Gly Pro Val Glu Glu Met Leu Ala Glu Val Asn Ala Thr Ile
305                 310                 315                 320

Thr Asp Ile Ile Ser Ala Leu Val Thr Ser Thr Phe Ile Ile Glu Lys
                325                 330                 335

Gln Pro Pro Gln Val Leu Lys Thr Gln Thr Lys Phe Ala Ala Thr Val
            340                 345                 350

Arg Leu Leu Val Gly Gly Lys Leu Asn Val His Met Asn Pro Pro Gln
            355                 360                 365

Val Lys Ala Thr Ile Ile Ser Glu Gln Gln Ala Lys Ser Leu Leu Lys
            370                 375                 380

Asn Glu Asn Thr Arg Asn Glu Cys Ser Gly Glu Ile Leu Asn Asn Cys
385                 390                 395                 400

Cys Val Met Glu Tyr His Gln Ala Thr Gly Thr Leu Ser Ala His Phe
                405                 410                 415

Arg Asn Met Ser Leu Lys Arg Ile Lys Arg Ala Asp Arg Arg Gly Ala
            420                 425                 430

Glu Ser Val Thr Glu Glu Lys Phe Thr Val Leu Phe Glu Ser Gln Phe
            435                 440                 445

Ser Val Gly Ser Asn Glu Leu Val Phe Gln Val Lys Thr Leu Ser Leu
            450                 455                 460

Pro Trp Val Ile Val His Gly Ser Gln Asp His Asn Ala Thr Ala Thr
465                 470                 475                 480

Val Leu Trp Asp Asn Ala Phe Ala Glu Pro Gly Arg Val Pro Phe Ala
                485                 490                 495

Val Pro Asp Lys Val Leu Trp Pro Gln Leu Cys Glu Ala Leu Asn Met
            500                 505                 510

Lys Phe Lys Ala Glu Val Gln Ser Asn Arg Gly Leu Thr Lys Glu Asn
            515                 520                 525

Leu Val Phe Leu Ala Gln Lys Leu Phe Asn Asn Ser Ser Ser His Leu
            530                 535                 540

Glu Asp Tyr Ser Gly Leu Ser Val Ser Trp Ser Gln Phe Asn Arg Glu
545                 550                 555                 560

Asn Leu Pro Gly Trp Asn Tyr Thr Phe Trp Gln Trp Phe Asp Gly Val
                565                 570                 575

Met Glu Val Leu Lys Lys His His Lys Pro His Trp Asn Asp Gly Ala
            580                 585                 590

Ile Leu Gly Phe Val Asn Lys Gln Gln Ala His Asp Leu Leu Ile Asn
            595                 600                 605

Lys Pro Asp Gly Thr Phe Leu Leu Arg Phe Ser Asp Ser Glu Ile Gly
            610                 615                 620

Gly Ile Thr Ile Ala Trp Lys Phe Asp Ser Pro Glu Arg Asn Leu Trp
625                 630                 635                 640

Asn Leu Lys Pro Phe Thr Thr Arg Asp Phe Ser Ile Arg Ser Leu Ala
                645                 650                 655

Asp Arg Leu Gly Asp Leu Ser Tyr Leu Ile Tyr Val Phe Pro Asp Arg
            660                 665                 670
```

-continued

```
Pro Lys Asp Glu Val Phe Ser Lys Tyr Tyr Thr Pro Val Leu Ala Lys
        675                 680                 685

Ala Val Asp Gly Tyr Val Lys Pro Gln Ile Lys Gln Trp Pro Glu Phe
    690                 695                 700

Val Asn Ala Ser Ala Asp Ala Gly Gly Ser Ser Ala Thr Tyr Met Asp
705                 710                 715                 720

Gln Ala Pro Ser Pro Ala Val Cys Pro Gln Ala Pro Tyr Asn Met Tyr
                725                 730                 735

Pro Gln Asn Pro Asp His Val Leu Asp Gln Asp Gly Glu Phe Asp Leu
            740                 745                 750

Asp Glu Thr Met Asp Val Ala Arg His Val Glu Glu Leu Leu Arg Arg
            755                 760                 765

Pro Met Asp Ser Leu Asp Ser Arg Leu Ser Pro Pro Ala Gly Leu Phe
    770                 775                 780

Thr Ser Ala Arg Gly Ser Leu Ser Leu Asp Ser Gln Arg Lys Leu Gln
785                 790                 795                 800

Phe Tyr Glu Asp Arg His Gln Leu Pro Ala Pro Lys Trp Ala Glu Leu
                805                 810                 815

Ala Asn Leu Ile Asn Asn Cys Met Asp Tyr Glu Pro Asp Phe Arg Pro
            820                 825                 830

Ser Phe Arg Ala Ile Ile Arg Asp Leu Asn Ser Leu Phe Thr Pro Asp
        835                 840                 845

Tyr Glu Leu Leu Thr Glu Asn Asp Met Leu Pro Asn Met Arg Ile Gly
    850                 855                 860

Ala Leu Gly Phe Ser Gly Ala Phe Glu Asp Arg Asp Pro Thr Gln Phe
865                 870                 875                 880

Glu Glu Arg His Leu Lys Phe Leu Gln Gln Leu Gly Lys Gly Asn Phe
                885                 890                 895

Gly Ser Val Glu Met Cys Arg Tyr Asp Pro Leu Gln Asp Asn Thr Gly
            900                 905                 910

Glu Trp Ala Val Lys Lys Leu Gln His Ser Thr Glu Glu His Leu Arg
        915                 920                 925

Asp Phe Glu Arg Glu Ile Glu Ile Leu Lys Ser Leu Gln His Asp Asn
    930                 935                 940

Ile Val Lys Tyr Lys Gly Val Cys Tyr Ser Ala Gly Arg Arg Asn Leu
945                 950                 955                 960

Lys Leu Ile Met Glu Tyr Leu Pro Tyr Gly Ser Leu Arg Asp Tyr Leu
                965                 970                 975

Gln Lys His Lys Glu Arg Ile Asp His Ile Lys Leu Leu Gln Tyr Thr
            980                 985                 990

Ser Gln Ile Cys Lys Gly Met Glu Tyr Leu Gly Thr Lys Arg Tyr Ile
        995                 1000                1005

His Arg Asp Leu Ala Thr Arg Asn Ile Leu Val Glu Asn Glu Asn
    1010                1015                1020

Arg Val Lys Ile Gly Asp Phe Gly Leu Thr Lys Val Leu Pro Gln
    1025                1030                1035

Asp Lys Glu Tyr Tyr Lys Val Lys Glu Pro Gly Glu Ser Pro Ile
    1040                1045                1050

Phe Trp Tyr Ala Pro Glu Ser Leu Thr Glu Ser Lys Phe Ser Val
    1055                1060                1065

Ala Ser Asp Val Trp Ser Phe Gly Trp Leu Tyr Glu Leu Phe Thr
    1070                1075                1080
```

-continued

```
Tyr Ile Glu Lys Ser Lys Ser Pro Pro Ala Glu Phe Met Arg Met
    1085            1090                1095

Ile Gly Asn Asp Lys Gln Gly Gln Met Ile Val Phe His Leu Ile
    1100            1105                1110

Glu Leu Leu Lys Asn Asn Gly Arg Leu Pro Arg Pro Asp Gly Cys
    1115            1120                1125

Pro Asp Glu Ile Tyr Met Ile Met Thr Glu Cys Trp Asn Asn Asn
    1130            1135                1140

Val Asn Gln Arg Pro Ser Phe Arg Asp Leu Ala Leu Arg Val Asp
    1145            1150                1155

Gln Ile Arg Asp Asn
    1160
```

LIVE CELL CONSTRUCTS FOR PRODUCTION OF CULTURED MILK PRODUCT AND METHODS USING THE SAME

CROSS-REFERENCE

This application claims the benefit of priority from U.S. Provisional Application No. 62/958,407, filed on Jan. 8, 2020, and U.S. Provisional Application No. 63/199,164, filed on Dec. 10, 2020, the contents of each are incorporated herein by reference in their entireties.

SEQUENCE LISTING

The instant application contains a Sequence Listing which has been submitted electronically in ASCII format and is hereby incorporated by reference in its entirety. Said ASCII copy, created on Jan. 14, 2021, is named BMQ-001_SL.txt and is 29,487 bytes in size.

FIELD OF THE INVENTION

This invention relates to live cell constructs and methods using the same for in vitro and/or ex vivo production of cultured milk product from cultured mammary cells.

BACKGROUND OF THE INVENTION

Milk is a staple of the human diet, both during infancy and throughout life. The American Academy of Pediatrics and World Health Organization recommend that infants be exclusively breastfed for the first 6 months of life, and consumption of dairy beyond infancy is a mainstay of human nutrition, representing a 700 billion dollar industry worldwide. However, lactation is a physiologically demanding and metabolically intensive process that can present biological and practical challenges for breastfeeding mothers, and milk production is associated with environmental, social, and animal welfare impacts in agricultural contexts.

The possibility of using mammalian cell culture to produce food has gained increasing interest in recent years, with the development of several successful prototypes of meat and sea food products from cultured muscle and fat cells (Stephens et al. 2018 *Trends Food Sci Technol.* 78:155-166). Additionally, efforts are underway to commercialize the production of egg and milk proteins using microbial expression systems. However, this fermentation-based process relies on the genetically engineered expression and purification of individual components and is unable to reproduce the full molecular profile of milk or dairy.

The present invention overcomes shortcomings in the art by providing live cell constructs and methods using the same for in vitro and/or ex vivo production of cultured milk product from cultured mammary cells.

SUMMARY OF THE INVENTION

Disclosed herein, in certain embodiments, are live cell constructs, comprising: (a) a three-dimensional scaffold having an exterior surface, an interior surface defining an interior cavity/basal chamber, and a plurality of pores extending from the interior surface to the exterior surface; (b) a matrix material disposed on the exterior surface of the three-dimensional scaffold; (c) a culture media disposed within the interior cavity/basal chamber and in fluidic contact with the internal surface; and (d) an at least 70% confluent monolayer of polarized mammary cells disposed on the matrix material, wherein the mammary cells are selected from the group consisting of: live primary mammary epithelial cells, live mammary myoepithelial cells, live mammary progenitor cells, live immortalized mammary epithelial cells, live immortalized mammary myoepithelial cells, and live immortalized mammary progenitor cells. In some embodiments, the polarized mammary cells comprise an apical surface and a basal surface. In some embodiments, the basal surface of the mammary cells is in fluidic contact with the culture media. In some embodiments, at least 70%, at least 80%, at least 90%, at least 95%, at least 99%, or 100% of the mammary cells are polarized in the same orientation. In some embodiments, the monolayer of polarized mammary cells is at least 70% confluent, at least 80% confluent, at least 90% confluent, at least 95% confluent, at least 99% confluent, or 100% confluent. In some embodiments, the mammary cells comprise a constitutively active prolactin receptor protein. In some embodiments, the culture medium comprises a carbon source, a chemical buffering system, one or more essential amino acids, one or more vitamins and/or cofactors, and one or more inorganic salts. In some embodiments, the culture medium further comprises prolactin. In some embodiments, the matrix material comprises one or more extracellular matrix proteins. In some embodiments, the three-dimensional scaffold comprises a natural polymer, a biocompatible synthetic polymer, a synthetic peptide, a composite derived from any of the preceding, or any combination thereof. In some embodiments, the natural polymer is collagen, chitosan, cellulose, agarose, alginate, gelatin, elastin, heparan sulfate, chondroitin sulfate, keratan sulfate, and/or hyaluronic acid. In some embodiments, the biocompatible synthetic polymer is polysulfone, polyvinylidene fluoride, polyethylene co-vinyl acetate, polyvinyl alcohol, sodium polyacrylate, an acrylate polymer, and/or polyethylene glycol.

Disclosed herein, in certain embodiments, are methods of producing an isolated cultured milk product from mammary cells, the method comprising: (a) culturing a live cell construct in a bioreactor under conditions which produce the cultured milk product, said live cell construct comprising: (i) a three-dimensional scaffold having an exterior surface, an interior surface defining an interior cavity/basal chamber, and a plurality of pores extending from the interior surface to the exterior surface; (ii) a matrix material disposed on the exterior surface of the three-dimensional scaffold; (iii) a culture media disposed within the interior cavity/basal chamber and in fluidic contact with the internal surface; and (iv) an at least 70% confluent monolayer of polarized mammary cells disposed on the matrix material, wherein the mammary cells are selected from the group consisting of: live primary mammary epithelial cells, live mammary myoepithelial cells, live mammary progenitor cells, live immortalized mammary epithelial cells, live immortalized mammary myoepithelial cells, and live immortalized mammary progenitor cells; and (b) isolating the cultured milk product. In some embodiments, the polarized mammary cells comprise an apical surface and a basal surface. In some embodiments, the basal surface of the mammary cells is in fluidic contact with the culture media. In some embodiments, the bioreactor is an enclosed bioreactor. In some embodiments, the bioreactor comprises an apical compartment that is substantially isolated from the internal cavity/basal chamber of the live cell construct. In some embodiments, the apical compartment is in fluidic contact with the apical surface of the mammary cells. In some embodiments, the cultured milk product is secreted from the apical surface of the mammary cells into the apical compartment. In some embodiments, the culture media substantially does not contact the cultured milk product. In some embodiments, the total cell density of mammary cells within the bioreactor is at least $10^{11}$. In some embodiments, the total surface area of mammary cells within the bioreactor is at least 1.5 m$^2$. In some embodiments, the culture medium comprises a carbon source, a chemical buffering system, one or more essential amino acids, one or more vitamins and/or cofactors, and one or more inorganic salts. In some embodiments, the matrix material comprises one or more extracellular matrix proteins. In some embodiments, the scaffold comprises a natural polymer, a biocompatible synthetic polymer, a synthetic peptide, a composite derived from any of the preceding, or any combination thereof. In some embodiments, the natural polymer is collagen, chitosan, cellulose, agarose, alginate, gelatin, elastin, heparan sulfate, chondroitin sulfate, keratan sulfate, and/or hyaluronic acid. In some embodiments, the biocompatible synthetic polymer is polysulfone, polyvinylidene fluoride, polyethylene co-vinyl acetate, polyvinyl alcohol, sodium polyacrylate, an acrylate polymer, and/or polyethylene glycol. In some embodiments, the culturing is carried out at a temperature of about 27° C. to about 39° C. In some embodiments, the culturing is carried out at a temperature of about 30° C. to about 37° C. In some embodiments, the culturing is carried out at an atmospheric concentration of $CO_2$ of about 4% to about 6%. In some embodiments, the culturing is carried out at an atmospheric concentration of $CO_2$ of about 5%.

Disclosed herein, in certain embodiments, are bioreactors, comprising: (a) an apical compartment comprising a cultured milk product; and (b) at least one live cell construct comprising: (i) a three-dimensional scaffold having an exterior surface, an interior surface defining an interior cavity/basal chamber, and a plurality of pores extending from the interior surface to the exterior surface; (ii) a matrix material disposed on the exterior surface of the three-dimensional scaffold; (iii) a culture media disposed within the interior cavity/basal chamber and in fluidic contact with the internal surface; and (iv) an at least 70% confluent monolayer of polarized mammary cells disposed on the matrix material, wherein the mammary cells are selected from the group consisting of: live primary mammary epithelial cells, live mammary myoepithelial cells, live mammary progenitor cells, live immortalized mammary epithelial cells, live immortalized mammary myoepithelial cells, and live immortalized mammary progenitor cells; wherein the apical surface of the mammary cells is in fluidic contact with the apical compartment. In some embodiments, the total cell density of mammary cells within the bioreactor is at least $10^{11}$. In some embodiments, the total surface area of mammary cells within the bioreactor is at least 1.5m$^2$.

Disclosed herein, in certain embodiments, are live cell constructs comprising mammary cells that compartmentalize feeding of the cells and secretion of cultured milk product.

Disclosed herein, in certain embodiments, are live cell constructs comprising, a scaffold having a top surface and a bottom surface; and a continuous monolayer of (a) live primary mammary epithelial cells, (b) a mixed population of live primary mammary epithelial cells, mammary myoepithelial cells and mammary progenitor cells, and/or (c) live immortalized mammary epithelial cells on the top surface of the scaffold, the continuous monolayer of (a) live primary mammary epithelial cells, (b) mixed population of live primary mammary epithelial cells, mammary myoepithelial cells and mammary progenitor cells, and/or (c) immortalized mammary epithelial cells having an apical surface and a basal surface (e.g., the cells form a polarized and confluent cell monolayer), wherein the construct comprises an apical compartment above and adjacent to the apical surface of the continuous monolayer of the (a) live primary mammary epithelial cells, the (b) mixed population of live primary mammary epithelial cells, mammary myoepithelial cells and mammary progenitor cells, and/or the (c) immortalized mammary epithelial cells and a basal compartment below and adjacent to the bottom surface of the scaffold.

Disclosed herein, in certain embodiments, are methods of producing milk in culture, the method comprising culturing the live cell construct of the present invention, thereby producing milk in culture.

Disclosed herein, in certain embodiments, are methods of making a live cell construct for producing milk in culture, the method comprising (a) isolating primary mammary epithelial cells, myoepithelial cells and/or mammary progenitor cells from mammary explants from mammary tissue (e.g., breast, udder, teat tissue), biopsy sample, or raw breastmilk, to produce isolated mammary epithelial cells, myoepithelial cells and mammary progenitor cells; (b) culturing the isolated primary mammary epithelial cells, myoepithelial cells and mammary progenitor cells to produce a mixed population of primary mammary epithelial cells, mammary myoepithelial cells and mammary progenitor cells; (c) cultivating the mixed population of (b) on a scaffold, the scaffold having an upper surface and lower surface, to produce a polarized, continuous (i.e., confluent) monolayer of primary mammary epithelial cells, myoepithelial cells and mammary progenitor cells of the mixed population on the upper surface of the scaffold, wherein the polarized, continuous monolayer comprises an apical surface and a basal surface, thereby producing a live cell construct for producing milk in culture.

Disclosed herein, in certain embodiments, are methods of making a live cell construct for producing milk in culture, the method comprising: a) isolating primary mammary epithelial cells, myoepithelial cells, and/or mammary progenitor cells from mammary explants from mammary tissue (e.g., breast, udder, teat tissue), biopsy sample, or raw breastmilk, to produce isolated mammary epithelial cells, myoepithelial cells, and/or mammary progenitor cells; (b) culturing the isolated primary mammary epithelial cells, myoepithelial cells, and/or mammary progenitor cells to produce a mixed population of primary mammary epithelial cells, mammary myoepithelial cells and mammary progenitor cells; (c) sorting the mixed population of primary mammary epithelial cells, myoepithelial cells, and/or mammary progenitor cells to produce a population of primary mammary epithelial cells; and (d) cultivating the population of primary mammary epithelial cells on a scaffold, the scaffold having an upper surface and lower surface, to produce a polarized, continuous (i.e., confluent) monolayer of primary mammary epithelial cells on the upper surface of the scaffold, wherein the polarized, continuous monolayer comprises an apical surface and a basal surface, thereby producing a live cell construct for producing milk in culture.

Disclosed herein, in certain embodiments, are methods of making a live cell construct for producing milk in culture, the method comprising (a) culturing immortalized mammary epithelial cells to produce increased numbers of immortalized mammary epithelial cells; (b) cultivating the immortalized mammary epithelial cells of (a) on a scaffold, the scaffold having an upper surface and lower surface, to produce a polarized, continuous (i.e., confluent) monolayer of immortalized mammary epithelial cells on the upper surface of the scaffold, wherein the polarized, continuous monolayer comprises an apical surface and a basal surface, thereby producing a live cell construct for producing milk in culture.

Disclosed herein, in certain embodiments, are methods of producing milk in culture comprising, culturing a live cell construct comprising (a) a scaffold comprising an upper surface and a lower surface and a continuous (i.e., confluent) polarized monolayer of live primary mammary epithelial cells, a continuous polarized monolayer of a mixed population of live primary mammary epithelial cells, mammary myoepithelial cells and mammary progenitor cells, and/or a continuous polarized monolayer of live immortalized mammary epithelial cells having an apical surface and a basal surface, wherein the continuous polarized monolayer of live primary mammary epithelial cells, the continuous polarized monolayer of the mixed population of live primary mammary epithelial cells, mammary myoepithelial cells and mammary progenitor cells and/or the continuous polarized monolayer of live immortalized mammary epithelial cells are located on the upper surface of the scaffold, (b) a basal compartment and an apical compartment, wherein the lower surface of the scaffold is adjacent to the basal compartment and the apical surface of the monolayer of live primary mammary epithelial cells, the monolayer of the mixed population of live primary mammary epithelial cells, mammary myoepithelial cells and mammary progenitor cells, and/or the monolayer of live immortalized mammary epithelial cells is adjacent to the apical compartment, wherein the monolayer of live primary epithelial mammary cells, the live primary epithelial mammary cells of the monolayer of the mixed population of live primary mammary epithelial cells, mammary myoepithelial cells and mammary progenitor cells, or the monolayer of immortalized mammary epithelial cells secretes milk through its apical surface into the apical compartment, thereby producing milk in culture.

Disclosed herein, in certain embodiments, are methods of producing a modified primary mammary epithelial cell or an immortalized mammary epithelial cell, wherein the method comprises introducing into the cell: (a) a polynucleotide encoding a prolactin receptor comprising a modified intracellular signaling domain, optionally wherein the prolactin receptor comprises a truncation wherein position 154 of exon 10 has been spliced to the 3' sequence of exon 11; (b) a polynucleotide encoding a chimeric prolactin receptor that binds to a ligand, which is capable of activating milk synthesis in the absence of prolactin; (c) a polynucleotide encoding a constitutively or conditionally active prolactin receptor protein, optionally wherein the polynucleotide encodes a constitutively active human prolactin receptor protein comprising a deletion of amino acids 9 through 187; (d) a polynucleotide encoding a modified (recombinant) effector of a prolactin protein comprising (i) a JAK2 tyrosine kinase domain fused to a STAT5 tyrosine kinase domain; and/or (ii) a prolactin receptor intracellular domain fused to a JAK2 tyrosine kinase domain; (e) a loss of function mutation into a circadian related gene PER2 (period circadian protein homolog 2); and/or (f) a polynucleotide encoding one or more glucose transporter genes GLUT1 and/or GLUT12, thereby increasing the rate of nutrient uptake at the basal surface of a monolayer of cells of the modified primary mammary epithelial cell or immortalized mammary epithelial cell.

DETAILED DESCRIPTION OF THE INVENTION

Figure 1:
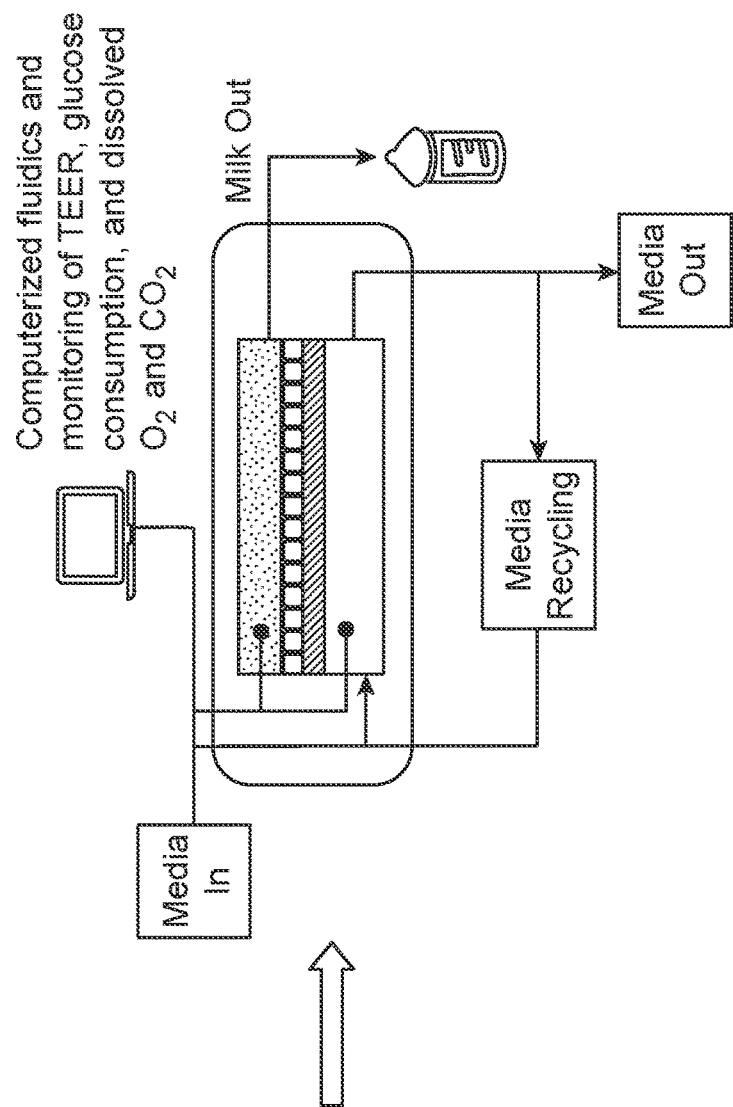
FIG. 1 shows an example of the collection of milk for nutritional use from mammary epithelial cells grown as a confluent monolayer in a compartmentalizing culture apparatus in which either fresh or recycled media is provided to the basal compartment and milk is collected from the apical compartment. TEER, transepithelial electrical resistance.
Figure 1:
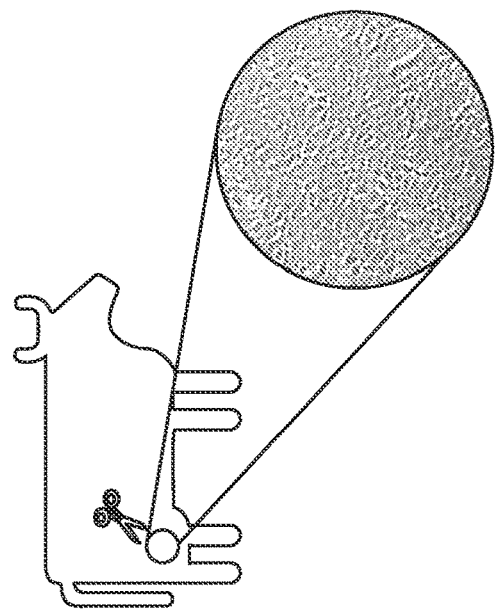

Milk is a nutrient-rich liquid food produced in the mammary glands of mammals. It is a primary source of nutrition for infant mammals (including humans who are breastfed) before they are able to digest other types of food. Human milk is not merely nutrition. Rather, human milk contains a variety of factors with bioactive qualities that have a profound role in infant survival and health. Natural milk contains many other macronutrients, including proteins, lipids, polysaccharides and lactose. Milk consumption occurs in two distinct overall types: a natural source of nutrition for all infant mammals and a food product.

In almost all mammals, milk is fed to infants through breastfeeding, either directly or by expressing the milk to be stored and consumed later. Early milk from mammals contains antibodies that provide protection to the newborn baby as well as nutrients and growth factors. Breast milk is not a uniform, unvarying, constant, factory-made product; rather, it is a biological product produced by women with markedly varying genotypes, phenotypes, and diets. To add to the complexity, the composition of breast milk is influenced by a myriad of maternal, infant, and environmental factors. Human milk contains a rich array of proteins, carbohydrates, lipids, fatty acids, minerals, and vitamins, but most of its disease-fighting potential comes from a plethora of antibodies, leukocytes, hormones, antimicrobial peptides, cytokines, chemokines, and other bioactive factors.

Mammary epithelial cells (MECs) in culture have been previously demonstrated to display organization and behavior similar to that observed in vivo (Arevalo et al. 2016 *Am J Physiol Cell Physiol.* 310(5) :C348-3 56; Chen et al. 2019 *Curr Protoc Cell Biol.* 82(1):e65). In Arevalo et al., specific biomarkers of MEC populations were detected in immortalized bovine mammary epithelial cells (BME-UV1) and immortalized bovine mammary alveolar cells (MAC-T) cultured on adherent 2-D plates, ultralow attachment surface 3D microplates, and 3D plates coated with Matrigel. Additionally, in Chen et al., protocols are detailed for isolation and culture of human primary mammary epithelial stem/progenitor cells from human breast tissue and subsequent generation of mammospheres using 3D organoid culture on gelatin sponges and Matrigel matrices. However, neither Arevalo nor Chen attempted to stimulate the production of milk from these MEC cultures.

In particular, when grown on an appropriate extracellular matrix and stimulated with prolactin, cultured bovine mammary epithelial cells polarize and organize into structures capable of secreting certain milk components (Blatchford et al. 1999 *Animal Cell Technology: Basic & Applied Aspects* 10:141-145). In Blatchford et al, bovine MECs polarized and formed mammospheres. Casein and butyrophilin were isolated from the cultures. However, the cells did not polarize in one uniform direction. Blatchford, et al. noted that the milk proteins were distributed in between the cells and dispersed throughout the mammospheres. Due to the lack of a uniform polarization orientation, Blatchford had to isolate the secreted proteins from the culture media.

Furthermore, in vitro two-dimensional models, such as those used in Blatchford et al. provide a low surface area-to-volume ratio (low density format). The surface area available for cell attachment limits the number of cells that can be grown The only known attempt to culture mouse mammary epithelial cells in a high-density format, such as the hollow fiber bioreactor, failed to achieve compartmentalization necessary for the production and extraction of a cultured milk product (Sharfstein et al. 1992 *Biotechnology and Bioengineering* 40:672-680). In Sharfstein et al., growth, long-term expression of functional differentiation, and metabolism of COMMA-1D (an immortalized mouse mammary epithelial cell line) was examined in two different systems: extended batch culture and hollow-fiber reactor culture. Using COMMA-1D seeded onto Costar Transwell® polycarbonate membrane cell culture inserts, Sharfstein et al. created a confluent monolayer capable of barrier formation and polarized metabolism between the apical and basal side that maintained gradients of glucose and lactate. However, using a hollow-fiber bioreactor culture, Sharfstein et al. was unable to achieve separation of basal and apical compartments. Furthermore, it was not determined if nutrient uptake was polarized in a hollow-fiber culture (Sharfstein et al. 1992). Importantly, no prior work has been able to culture mammary epithelial cells from humans or other nutritionally relevant species in a high-density, three-dimensional, compartmentalizing format.

Disclosed herein, in certain embodiments, are live cell constructs, methods of making the same, and methods of using the same for in vitro and/or ex vivo production of cultured milk product from cultured mammary cells.

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features described herein can be used in any combination. Moreover in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Definitions

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

Moreover, any feature or combination of features set forth herein can be excluded or omitted.

The term "about," as used herein when referring to a measurable value such as an amount of a compound or agent, dose, time, temperature, and the like, is meant to encompass variations of ±10%, ±5%, ±1%, ±0.5%, or even ±0.1% of the specified amount.

Unless otherwise defined, all technical and scientific terms used herein have the same meaning as commonly understood by one of ordinary skill in the art. The terminology used in the description herein is for the purpose of describing particular embodiments only and is not intended to be limiting.

Nucleotide sequences are presented herein by single strand only, in the 5' to 3' direction, from left to right, unless specifically indicated otherwise. Nucleotides and amino acids are represented herein in the manner recommended by the IUPAC-1UB Biochemical Nomenclature Commission, or (for amino acids) by either the one-letter code, or the three letter code, both in accordance with 37 C.F.R. § 1.822 and established usage.

Except as otherwise indicated, standard methods known to those skilled in the art may be used for production of recombinant and synthetic polypeptides, antibodies or antigen-binding fragments thereof, manipulation of nucleic acid sequences, production of transformed cells, the construction of viral vector constructs, and transiently and stably transfected packaging cells. Such techniques are known to those skilled in the art. See, e.g., Sambrook et al., Molecular Cloning: A Laboratory Manual 2nd Ed. (Cold Spring Harbor, NY, 1989); F. M. Ausubel et al. Current Protocols In Molecular Biology (Green Publishing Associates, Inc. and John Wiley & Sons, Inc., New York).

As used herein, the transitional phrase "consisting essentially of" is to be interpreted as encompassing the recited materials or steps and those that do not materially affect the basic and novel characteristic(s) of the claimed invention. Thus, the term "consisting essentially of" as used herein should not be interpreted as equivalent to "comprising."

As used herein, the term "polypeptide" encompasses both peptides and proteins, and does not require any particular amino acid length or tertiary structure unless indicated otherwise.

The term "polarized" as used herein in reference to cells and/or monolayers of cells refers to a spatial status of the cell wherein there are two distinct surfaces of the cell, e.g., an apical surface and a basal surface, which may be different. In some embodiments, the distinct surfaces of a polarized cell comprises different surface and/or transmembrane receptors and/or other structures. In some embodiments, individual polarized cells in a continuous monolayer have similarly-oriented apical surfaces and basal surfaces. In some embodiments, individual polarized cells in a continuous monolayer have communicative structures between individual cells (e.g., tight junctions) to allow cross communication between individual cells and to create separation (e.g., compartmentalization) of the apical compartment and basal compartment.

As used herein, "apical surface" means the surface of a cell that faces an external environment or toward a cavity or chamber, for example the cavity of an internal organ. With respect to mammary epithelial cells, the apical surface is the surface from which the cultured milk product is secreted.

As used herein, "basal surface" means the surface of a cell that is in contact with a surface, e.g., the matrix of a bioreactor.

As used herein, "bioreactor" means a device or system that supports a biologically active environment that enables the production of a culture milk product described herein from mammary cells described herein.

The term "lactogenic" as used herein refers to the ability to stimulate production and/or secretion of milk. A gene or protein (e.g., prolactin) may be lactogenic, as may any other natural and/or synthetic product. In some embodiments, a lactogenic culture medium comprises prolactin, thereby stimulating production of milk by cells in contact with the culture medium.

As used herein, the term "food grade" refers to materials considered non-toxic and safe for consumption (e.g., human and/or other animal consumption), e.g., as regulated by standards set by the U.S. Food and Drug Administration.

In some embodiments, milk produced by the primary mammary epithelial cells (e.g., primary mammary epithelial cells from the isolated live primary mammary epithelial cells and/or the primary mammary epithelial cells from the mixed population of live primary mammary epithelial cells, mammary myoepithelial cells and/or mammary progenitor cells) or the immortalized mammary epithelial cells is secreted through the apical surface of the cells into the apical compartment. In some embodiments, a basal compartment comprises a culture medium and the culture medium is in contact with the basal surface of the live primary mammary epithelial cells, the mixed population of live primary mammary epithelial cells, mammary myoepithelial cells and mammary progenitor cells, and/or the immortalized mammary epithelial cells.

Live Cell Constructs

Disclosed herein, in certain embodiments, are live cell constructs for producing milk in culture, the live cell constructs comprising a continuous monolayer of live mammary cells selected from the group consisting of: (a) live primary mammary epithelial cells, (b) live mammary myoepithelial cells, (c) live mammary progenitor cells, and/or (d) live immortalized mammary epithelial cells.

In some embodiments, the mammary cells comprise milk-producing mammary epithelial cells, contractile myoepithelial cells, and/or progenitor cells that can give rise to both mammary epithelial and mammary contractile myoepithelial cells. Mammary epithelial cells are the only cells that produce milk. In some embodiments, the mammary cells comprise mammary epithelial cells, primary mammary epithelial cells, mammary myoepithelial cells and mammary progenitor cells.

In some embodiments, the mammary cells are from breast tissue, udder tissue, and/or teat tissue of a mammal. In some embodiments, the mammary cells are from any mammal, e.g., a primate (e.g., chimpanzee, orangutan, gorilla, monkey (e.g., Old World, New World), lemur, human), a dog, a cat, a rabbit, a mouse, a rat, a horse, a cow, a goat, a sheep, an ox (e.g., Bos spp.), a pig, a deer, a musk deer, a bovid, a whale, a dolphin, a hippopotamus, an elephant, a rhinoceros, a giraffe, a zebra, a lion, a cheetah, a tiger, a panda, a red panda, and an otter. In some embodiments, the mammary cells are from an endangered species, e.g., an endangered mammal. In some embodiments, the mammary cells are from a human. In some embodiments, the mammary cells are from a bovid (e.g., a cow).

In some embodiments, the continuous monolayer of live mammary cells is derived from breast milk-derived stem cells or breast stem cells originating from tissue biopsy of the mammary gland. The epithelial component of breast milk includes not only mature epithelial cells, but also their precursors and stem cells in culture. A subpopulation of breast milk-derived stem cells displays very high multilineage potential, resembling those typical for human embryonic stem cells (hESCs). Breast stem cells may also originate from tissue biopsy of the mammary gland, and include terminally differentiated MECs. Both breast milk-derived stem cells and breast stem cells originating from tissue biopsy of the mammary gland are multi-potent cells that can give rise to MECs or myoepithelial cells.

In some embodiments, at least 50% of the mammary cells of the live cells culture are polarized. In some embodiments, at least 55% of the mammary cells of the live cells culture are polarized. In some embodiments, at least 60% of the mammary cells of the live cells culture are polarized. In some embodiments, at least 65% of the mammary cells of the live cells culture are polarized. In some embodiments, at least 70% of the mammary cells of the live cells culture are polarized. In some embodiments, at least 75% of the mammary cells of the live cells culture are polarized. In some embodiments, at least 80% of the mammary cells of the live cells culture are polarized. In some embodiments, at least 85% of the mammary cells of the live cells culture are polarized. In some embodiments, at least 90% of the mammary cells of the live cells culture are polarized. In some embodiments, at least 95% of the mammary cells of the live cells culture are polarized. In some embodiments, at least 100% of the mammary cells of the live cells culture are polarized. In some embodiments, substantially all of the mammary cells of the live cell construct are polarized (i.e., have an apical surface and a basal surface). In some embodiments, substantially all of the mammary cells of the live cell construct are polarized and substantially all of the polarized cells are oriented in the same direction. For example, in some embodiments, substantially all of the mammary cells have an apical surface and a basal surface, wherein the apical surface of substantially all of the cells is oriented in the same direction and the basal surface of substantially all of the cells is oriented in the same direction.

In some embodiments, the monolayer of epithelial mammary cells has at least 70% confluence over the scaffold. In some embodiments, the monolayer of mammary epithelial cells has at least about 75% confluence over the scaffold. In some embodiments, the monolayer of epithelial mammary cells has at least about 80% confluence over the scaffold. In some embodiments, the monolayer of epithelial mammary cells has at least about 85% confluence over the scaffold. In some embodiments, the monolayer of epithelial mammary cells has at least about 90% confluence over the scaffold. In some embodiments, monolayer of epithelial mammary cells has at least about 95% confluence over the scaffold. In some embodiments, the monolayer of epithelial mammary cells has at least about 99% confluence over the scaffold. In some embodiments, the monolayer of epithelial mammary cells has 100% confluence over the scaffold.

Genetic Modifications to Mammary Cells

In some embodiments, the mammary cells comprise a constitutively active prolactin receptor protein. In some embodiments, the mammary cells comprise a constitutively active human prolactin receptor protein. Where the primary mammary epithelial cell or immortalized mammary epithelial cells comprise a constitutively active prolactin receptor, the culture medium does not contain prolactin.

In some embodiments, the constitutively active human prolactin receptor protein comprises a deletion of amino acids 9 through 187, wherein the numbering is based on the reference amino acid sequence of a human prolactin receptor identified as SEQ ID NO: 1.

```
SEQ ID NO: 1: Human prolactin receptor (GenBank
accession number AAD32032.1)
MKENVASATVFTLLLFLNTCLLNGQLPPGKPEIFKCRSPNKETFTCWWRP

GTDGGLPTNYSLTYHREGETLMHECPDYITGGPNSCHFGKQYTSMWRTYI

MMVNATNQMGSSFSDELYVDVTYIVQPDPPLELAVEVKQPEDRKPYLWIK

WSPPTLIDLKTGWFTLLYEIRLKPEKAAEWEIHFAGQQTEFKILSLHPGQ

KYLVQVRCKPDHGYWSAWSPATFIQIPSDFTMNDTTVWISVAVLSAVICL

IIVWAVALKGYSMVTCIFPPVPGPKIKGFDAHLLEKGKSEELLSALGCQD

FPPTSDYEDLLVEYLEVDDSEDQHLMSVHSKEHPSQGMKPTYLDPDTDSG

RGSCDSPSLLSEKCEEPQANPSTFYDPEVIEKPENPETTHTWDPQCISME

GKIPYFHAGGSKCSTWPLPQPSQHNPRSSYHNITDVCELAVGPAGAPATL

LNEAGKDALKSSQTIKSREEGKATQQREVESFHSETDQDTPWLLPQEKTP

FGSAKPLDYVEIHKVNKDGALSLLPKQRENSGKPKKPGTPENNKEYAKVS

GVMDNNILVLVPDPHAKNVACFEESAKEAPPSLEQNQAEKALANFTATSS

KCRLQLGGLDYLDPACFTHSFH
```

In some embodiments, the constitutively active human prolactin receptor protein comprising a deletion of the following amino acids:

```
VFTLLLFLNTCLLNGQLPPGKPEIFKCRSPNKETFTCWWRPGTDGGLPTN

YSLTYHREGETLMHECPDYITGGPNSCHFGKQYTSMWRTYIMMVNATNQM

GSSFSDELYVDVTYIVQPDPPLELAVEVKQPEDRKPYLWIKWSPPTLIDL

KTGWFTLLYEIRLKPEKAA (e.g., amino acid positions 10 through 178 of SEQ ID NO: 1).
```

In some embodiments, the mammary cells comprise a loss of function mutation introduced into a circadian related gene PER2. In some embodiments, the loss of function mutation introduced into a circadian related gene PER2 promotes increased synthesis of cultured milk components. In some embodiments, the loss of function mutation in the PER2 gene comprises an 87-amino acid deletion from position 348 to 434 in PER2, wherein the numbering is based on the reference amino acid seauence of a human PER2 identified as SEO ID NO:2.

```
SEQ ID NO: 2: Human Period circadian protein homo-
log 2 (GenBank accession number NM_022817)
MNGYAEFPPSPSNPTKEPVEPQPSQVPLQEDVDMSSGSSGHETNENCSTG

RDSQGSDCDDSGKJELGMLVEPPDARQSPDTFSLMMAKSEHNPSTSGCSS

DQSSKVDTHKEL1KTLKELKVHLPADKKAKGKASTLATLKYALRSVKQVK

ANEEYYQLLMSSEGHPCGADVPSYTVEEMESVTSEHIVKNADMFAVAVSL

VSGKILYISDQVASIFHCKRDAFSDAKFVEFLAPHDVGVFHSFTSPYKLP

LWSMCSGADSFTQECMEEKSFFCRVSVRKSHENEIRYHPFRMTPYLVKVR

DQQGAESQLCCLLLAERVHSGYEAPRIPPEKRIFTTTHTPNCLFQDVDER

AVPLLGYLPQDLIETPVLVQLHPSDRPLMLAIHKKILQSGGQPFDYSPIR

FRARNGEYITLDTSWSSFINPWSRKISFIIGRHKVRVGPLNEDVFAAHPC

TEEKALHPSIQELTEQIHRLLLQPVPHSGSSGYGSLGSNGSHEHLMSQTS

SSDSNGHEDSRRRRAEICKNGNKTKNRSHYSHESGEQKKKSVTEMQTNPP

AEKKAVPAMEKDSLGVSFPEELACKNQPTCSYQQISCLDSVIRYLESCNE

AATLKRKCEFPANVPALRSSDKRKATVSPGPHAGEAEPPSRVNSRTGVGT

HLTSLALPGKAESVASLTSQCSYSSTIVHVGDKKPQPELEMVEDAASGPE

SLDCLAGPALACGLSQEKEPFKKLGLTKEVLAAHTQKEEQSFLQKFKEIR

KLSIFQSHCHYYLQERSKGQPSERTAPGLRNTSGIDSPWKKTGKNRKLKS

KRVKPRDSSESTGSGGPVSARPPLVGLNATAWSPSDTSQSSCPAVPFPAP

VPAAYSLPVFPAPGTVAAPPAPPHASFTVPAVPVDLQHQFAVQPPPFPAP

LAPVMAFMLPSYSFPSGTPNLPQAFFPSQPQFPSHPTLTSEMASASQPEF

PEGGTGAMGTTGATETAAVGADCKPGTSRDQQPKAPLTRDEPSDTQNSDA

LSTSSGLLNLLLNEDLCSASGSAASESLGSGSLGCDASPSGAGSSDTSHT

SKYFGSIDSSENNHKAKMNTGMEESEHFIKCVLQDPIWLLMADADSSVMM

TYQLPSRNLEAVLKEDREKLKLLQKLQPRFTESQKQELREVHQWMQTGGL

PAAIDVAECVYCENKEKGNICIPYEEDIPSLGLSEVSDTKEDENGSPLNH

RIEEQT
```

In some embodiments, the loss of function mutation introduced into PER2 comprises a deletion of the following amino acids:

CLFQDVDERAVPLLGYLPQDLIETPVLVQLHPSDRPLMLAIHKKILQSGG

QPFDYSPIRFRARNGEYITLDTSWSSFINPWSRKISFIIGRHKV (e.g., amino acid positions 341 through 434 of SEQ ID NO: 2).

In some embodiments, the mammary cells comprise a polynucleotide encoding a prolactin receptor comprising a modified intracellular signaling domain. In some embodiments, the loss of function mutation introduced into a circadian related gene PER2 promotes increased synthesis of individual cultured milk components. In some embodiments, the prolactin receptor comprises a truncation wherein position 154 of exon 10 has been spliced to the 3' sequence of exon 11. In some embodiments, the prolactin receptor comprises a sequence according to SEQ ID NO: 3.

SEQ ID NO: 3: Human isoform 4 of Prolactin receptor (GenBank accession number AF416619; Trott et al. 2003 J. Mol. Endocrinol 3Q(1): 31-47)
MKENVASATVFTLLLFLNTCLLNGQLPPGKPEIFKCRSPNKETFTCWWRP

GTDGGLPTNYSLTYHREGETLMHECPDYITGGPNSCHFGKQYTSMWRTYI

MMVNATNQMGSSFSDELYVDVTYIVQPDPPLELAVEVKQPEDRKPYLWIK

WSPPTLIDLKTGWFTLLYEIRLKPEKAAEWEIHFAGQQTEFKILSLHPGQ

KYLVQVRCKPDHGYWSAWSPATFIQIPSDFTMNDTTVWISVAVLSAVICL

IIVWAVALKGYSMVTCIFPPVPGPKIKGFDAHLLEKGKSEELLSALGCQD

FPPTSDYEDLLVEYLEVDDSEDQHLMSVHSKEHPSQGDPLMLGASHYKNL

KSYRPRKISSQGRLAVFTKATLTTVQ

In some embodiments, the mammary cells comprise a polynucleotide encoding a modified (e.g., recombinant) effector of a prolactin protein. In some embodiments, the modified effector of the prolactin protein comprises a janus kinase-2 (JAK2) tyrosine kinase domain. In some embodiments, the modified effector comprises a JAK2 tyrosine kinase domain fused to a signal transducer and activator of transcription-5 (STAT5) tyrosine kinase domain (e.g., a polynucleotide encoding a JAK2 tyrosine kinase domain linked to the 3' end of a polynucleotide encoding the STAT5 tyrosine kinase domain). In some embodiments, the modified effector of a prolactin protein promotes increased synthesis of individual cultured milk components. In some embodiments, the modified effector has a sequence according to SEQ ID NO: 4. Bolded amino acids correspond to the JAK2 kinase domain of amino acid positions 757 through 1129 of a reference human JAK2 amino acid sequence.

SEQ ID NO: 4. STA5A Human signal transducer and activator of transcription 5A fused at 3' end to amino acids 757-1129 of JAK2 human tyrosine-protein kinase
MAGWIQAQQL QGDALRQMQV LYGQHFPIEV RHYLAQWIES

QPWDAIDLDN PQDRAQATQL LEGLVQELQK KAEHQVGEDG

FLLKIKLGHY ATQLQKTYDR CPLELVRCIR HILYNEQRLV

REANNCSSPA GILVDAMSQK HLQINQTFEE LRLVTQDTEN

ELKKLQQTQE YFIIQYQESL RIQAFAQLA QLSPQERLSR

ETALQQKQVS LEAWLQREAQ TLQQYRVELA EKHQKTLQLL

RKQQTIILDD ELIQWKRRQQ LAGNGGPPEG SLDVLQSWCE

KLAEIIWQNR QQIRRAEHLC QQLPIPGPVE EMLAEVNATI

TDIISALVTS TFIIEKQPPQ VLKTQTKFAA TVRLLVGGKL

NVHMNPPQVK ATIISEQQAK SLLKNENTRN ECSGEILNNC

CVMEYHQATG TLSAHFRNMS LKRIKRADRR GAESVTEEKF

TVLFESQFSV GSNELVFQVK TLSLPWVIV HGSQDHNATA

TVLWDNAFAE PGRVPFAVPD KVLWPQLCEA LNMKFKAEVQ

SNRGLTKENL VFLAQKLFNN SSSHLEDYSG LSVSWSQFNR

ENLPGWNYTF WQWFDGVMEV LKKHHKPHWN DGAILGFVNK

QQAHDLLINK PDGTFLLRFS DSEIGGITIA WKFDSPERNL

WNLKPFTTRD FSIRSLADRL GDLSYLIYVF PDRPKDEVFS

KYYTPVLAKA VDGYVKPQIK QWPEFVNAS ADAGGSSATY

MDQAPSPAVC PQAPYNMYPQ NPDHVLDQDG EFDLDETMDV

ARHVEELLRR PMDSLDSRLS PPAGLFTSAR GSLSLDSQ

RKLQFYEDRH QLPAPKWAEL ANLINNCMDY EPDFRPSFRA

IIRDLNSLFT PDYELLTEND MLPNMRIGAL GFSGAFEDRD

PTQFEERHLK FLQQLGKGNF GSVEMCRYDP LQDNTGEWA

VKKLQHSTEE HLRDFEREIE ILKSLQHDNI VKYKGVCYSA

GRRNLKLIME YLPYGSLRDY LQKHKERIDH IKLLQYTSQI

CKGMEYLGTK RYIHRDLATR NILVENENRV KIGDFGLTKV

LPQDKEYYKV KEPGESPIFW YAPESLTESK FSVASDVWSF

GWLYELFTY IEKSKSPPAE FMRMIGNDKQ GQMIVFHLIE

LLKNNGRLPR PDGCPDEIYM IMTECWNNNV NQRPSFRDLA

LRVDQIRDN.

In some embodiments, the mammary cells are immortalized. In some embodiments, the mammary cells comprise one or more nucleic acids encoding human telomerase reverse transcriptase (hTERT) or simian virus 40 (SV40). In some embodiments, the mammary cells comprise a small hairpin RNA (shRNA) to p16 (Inhibitor of Cyclin-Dependent Kinase 4) (p16(INK4)) and Master Regulator of Cell Cycle Entry and Proliferative Metabolism (c-MYC).

In some embodiments, the method comprises introducing into the cell: (a) a polynucleotide encoding a prolactin receptor comprising a modified intracellular signaling domain, optionally wherein the prolactin receptor comprises a truncation wherein position 154 of exon 10 has been spliced to the 3' sequence of exon 11; (b) a polynucleotide encoding a chimeric prolactin receptor that binds to a ligand, which is capable of activating milk synthesis in the absence of prolactin; (c) a polynucleotide encoding a constitutively or conditionally active prolactin receptor protein, optionally wherein the polynucleotide encodes a constitutively active human prolactin receptor protein comprising a deletion of amino acids 9 through 187 (e.g., a deletion of amino acids 9 through 187, wherein the numbering is based on the reference amino acid sequence of a human prolactin receptor identified as SEQ ID NO: 1); (d) a polynucleotide encoding a modified (e.g., recombinant) effector of a prolactin protein comprising (i) a janus kinase-2 (JAK2) tyrosine kinase domain, optionally wherein the JAK2 tyrosine kinase domain is fused to a signal transducer and activator of transcription-5 (STAT5) tyrosine kinase domain (e.g., a polynucleotide encoding a JAK2 tyrosine kinase domain linked to the 3' end of a polynucleotide encoding the STAT5 tyrosine kinase domain); and/or (ii) a prolactin receptor intracellular domain fused to a JAK2 tyrosine kinase domain; (e) a loss of function mutation into a circadian related gene PER2 (period circadian protein homolog 2); and/or (f) a polynucleotide encoding one or more glucose transporter genes GLUT1 and/or GLUT12, thereby increasing the rate of nutrient uptake at the basal surface of the monolayer.

Scaffolds

In some embodiments, the live cell construct further comprises a scaffold having a top surface/exterior surface and a bottom surface/interior surface. In some embodiments, the scaffold is a 2-dimensional surface or a 3-dimensional surface (e.g., a 3-dimensional micropatterned surface, and/or as a cylindrical structure that is assembled into bundles). A non-limiting example of a 2-dimensional surface scaffold is a Transwell® filter. In some embodiments, the scaffold is a 3-dimensional surface. Non-limiting examples of a 3-dimensional micropatterned surface include a microstructured bioreactor, a decellularized tissue (e.g., a decellularized mammary gland or decellularized plant tissue), micropatterned scaffolds fabricated through casting or three-dimensional printing with biological or biocompatible materials, textured surface. In some embodiments, the scaffold is produced by electrospinning cellulose nanofibers and/or a cylindrical structure that can be assembled into bundles (e.g., a hollow fiber bioreactor). In some embodiments, the scaffold is porous. In some embodiments, the scaffold is a 3D scaffold. In some embodiments, the 3-dimensional scaffold is any structure which has an enclosed hollow interior/central cavity. In some embodiments, the three dimensional scaffold joins with one or more surfaces to form an enclosed interior chamber/basal compartment. For example, the scaffold can join with one or more walls of a bioreactor to form the interior chamber/basal compartment. In some embodiments, the scaffold is a hollow fiber bioreactor. In some embodiments, the 3D scaffold is a tube in which the central cavity is defined by the interior surface of the scaffold. In some embodiments, the 3D scaffold is a hollow sphere in which the central cavity is defined by the interior surface of the scaffold.

For in vitro culture methods for studies of intestinal absorption, 2-dimensional surface scaffold such as Transwells® have long been used as the standard as they provide both apical and basolateral spaces to simulate the gut-blood-barrier and enable both active and passive transport of drugs and nutrients. However, cells seeded onto flat supports exhibit markedly different phenotypes to cells in vivo, partly due to the poor representation of the 3-D extracellular microenvironments.

A 3-dimensional scaffold allows mammary cells (e.g., MECs) to grow or interact with their surroundings in all three dimensions. Unlike 2D environments, a 3D cell culture allows cells in vitro to grow in all directions, approximating the in vivo mammary environment. Further, the 3D scaffold allows for a larger surface area for culture of the cells and for metabolite and gas exchange, plus it enables necessary compartmentalization—enabling the cultured milk product to be secreted into one compartment, while the cell culture media is contacted with the mammary cells in another compartment. To date, a confluent monolayer with polarized separation of basal and apical cell surfaces using mammary epithelial cell on a 3D surface has not been achieved (Sharfstein et al. 1992).

In some embodiments, the scaffold is porous. In some embodiments, the scaffold is permeable to the cell media, allowing the cell media to contact the cells of the cell monolayer. In some embodiments, the scaffold is transversed by at least one pore that allows the cell media to contact the basal surface of the cells of the cell monolayer.

In some embodiments, the top surface/exterior surface of the scaffold is coated with a matrix material. In some embodiments, the matrix is made up of one or more extracellular matrix proteins. Non-limiting examples of extracellular matrix proteins include collagen, laminin, entactin, tenascin, and/or fibronectin. In some embodiments, the scaffold comprises a natural polymer, a biocompatible synthetic polymer, a synthetic peptide, and/or a composite derived from any combination thereof. In some embodiments, a natural polymer useful with this invention includes, but is not limited to, collagen, chitosan, cellulose, agarose, alginate, gelatin, elastin, heparan sulfate, chondroitin sulfate, keratan sulfate, and/or hyaluronic acid. In some embodiments, a biocompatible synthetic polymer useful with this invention includes, but is not limited to, cellulose, polysulfone, polyvinylidene fluoride, polyethylene co-vinyl acetate, polyvinyl alcohol, sodium polyacrylate, an acrylate polymer, and/or polyethylene glycol. In some embodiments, the top of the scaffold is coated with laminin and collagen.

In some embodiments, the matrix material is porous. In some embodiments, the matrix material is permeable to the cell media, allowing the cell media to contact the cells of the cell monolayer. In some embodiments, the matrix material is transversed by at least one pore that allows the cell media to contact the basal surface of the cells of the cell monolayer.

In some embodiments, the pore size of the scaffold and/or matrix material is at least about 0.1 µm. In some embodiments, the pore size of the scaffold and/or matrix material is at least about 0.2 µm. In some embodiments, the pore size of the scaffold and/or matrix material is at least about 0.3 µm. In some embodiments, the pore size of the scaffold and/or matrix material is at least about 0.4 µm. In some embodiments, the pore size of the scaffold and/or matrix material is at least about 0.5 µm. In some embodiments, the pore size of the scaffold and/or matrix material is at least about 0.6 µm. In some embodiments, the pore size of the scaffold and/or matrix material is at least about 0.7 µm. In some embodiments, the pore size of the scaffold and/or matrix material is at least about 0.8 µm. In some embodiments, the pore size of the scaffold and/or matrix material is at least about 0.9 µm. In some embodiments, the pore size of the scaffold and/or matrix material is at least about 1.0 µm. In some embodiments, the pore size of the scaffold and/or matrix material is at least about 1.1 µm. In some embodiments, the pore size of the scaffold and/or matrix material is at least about 1.2 µm. In some embodiments, the pore size of the scaffold and/or matrix material is at least about 1.3 µm. In some embodiments, the pore size of the scaffold and/or matrix material is at least about 1.4 µm. In some embodiments, the pore size of the scaffold and/or matrix material is at least about 1.5 µm. In some embodiments, the pore size of the scaffold and/or matrix material is at least about 1.6 µm. In some embodiments, the pore size of the scaffold and/or matrix material is at least about 1.7 µm. In some embodiments, the pore size of the scaffold and/or matrix material is at least about 1.8 µm. In some embodiments, the pore size of the scaffold and/or matrix material is at least about 1.9 µm. In some embodiments, the pore size of the scaffold and/or matrix material is at least about 2.0 µm. In some embodiments, the pore size of the scaffold and/or matrix material is at least about 2.1 µm. In some embodiments, the pore size of the scaffold and/or matrix material is at least about 2.2 µm. In some embodiments, the pore size of the scaffold and/or matrix material is at least about 2.2 µm. In some embodiments, the pore size of the scaffold and/or matrix material is at least about 2.3 µm. In some embodiments, the pore size of the scaffold and/or matrix material is at least about 2.4 µm. In some embodiments, the pore size of the scaffold and/or matrix material is at least about 2.5 µm. In some embodiments, the pore size of the scaffold and/or matrix material is at least about 2.6 µm. In some embodiments, the pore size of the scaffold and/or matrix material is at least about 2.7 µm. In some embodiments, the pore size of the scaffold and/or matrix material is at least about 2.8 µm. In some embodiments, the pore size of the scaffold and/or matrix material is at least about 2.9 µm. In some embodiments, the pore size of the scaffold and/or matrix material is at least about 3.0 µm.

In some embodiments, the live cell construct comprises a scaffold having a top surface/exterior surface and a bottom surface/interior surface; and a continuous monolayer of (a) live primary mammary epithelial cells, (b) a mixed population of live primary mammary epithelial cells, mammary myoepithelial cells and mammary progenitor cells, and/or (c) live immortalized mammary epithelial cells on the top surface of the scaffold, the continuous monolayer of (a) live primary mammary epithelial cells, (b) mixed population of live primary mammary epithelial cells mammary myoepithelial cells and mammary progenitor cells, and/or (c) immortalized mammary epithelial cells having an apical surface and a basal surface (e.g., the cells form a polarized and confluent cell monolayer), wherein the construct comprises an apical compartment above and adjacent to the apical surface of the continuous monolayer of the (a) live primary mammary epithelial cells, the (b) mixed population of live primary mammary epithelial cells, mammary myoepithelial cell and mammary progenitor cells, and/or the (c) immortalized mammary epithelial cells and a basal compartment below and adjacent to the bottom surface of the scaffold.

Bioreactor

Disclosed herein, in certain embodiments, are bioreactors, comprising: (a) an apical compartment comprising a cultured milk product; and (b) at least one live cell construct comprising: (i) a three-dimensional scaffold having an exterior surface, an interior surface defining an interior cavity/basal chamber, and a plurality of pores extending from the interior surface to the exterior surface; (ii) a matrix material disposed on the exterior surface of the three-dimensional scaffold; (iii) a culture media disposed within the interior cavity/basal chamber and in fluidic contact with the internal surface; and (iv) an at least 70% confluent monolayer of polarized mammary cells disposed on the matrix material, wherein the mammary cells are selected from the group consisting of: live primary mammary epithelial cells, live mammary myoepithelial cells, live mammary progenitor cells, live immortalized mammary epithelial cells, live immortalized mammary myoepithelial cells, and live immortalized mammary progenitor cells; wherein the apical surface of the mammary cells is in fluidic contact with the apical compartment.

In some embodiments, the bioreactor is an enclosed bioreactor. In some embodiments, the apical chamber is substantially isolated from the interior cavity/basal compartment.

A hollow fiber bioreactor is an exemplary bioreactor for use with the methods disclosed here. The hollow fiber bioreactor is a high-density, continuous perfusion culture system that closely approximates the environment in which cells grow in vivo. It consists of thousands of semi-permeable 3D scaffolds (i.e., hollow fibers) in a parallel array within a cartridge shell fitted with inlet and outlet ports. These fiber bundles are potted or sealed at each end so that any liquid entering the ends of the cartridge will necessarily flow through the interior of the fibers. Cells are generally seeded outside the fibers within the cartridge in the extra capillary space (ECS).

Three fundamental characteristics differentiate hollow fiber cell culture from other methods: (1) cells are bound to a porous matrix much as they are in vivo, not a plastic dish, microcarrier or other impermeable support, (2) the molecular weight cut off of the support matrix can be controlled, and (3) extremely high surface area to volume ratio (150 cm$^2$ or more per mL) which provides a large area for metabolite and gas exchange for efficient growth of host cells.

The bioreactor structure provides a fiber matrix that allows permeation of nutrients, gases and other basic media components, as well as cell waste products, but not cells, where the cells can be amplified. Hollow fiber bioreactor technology has been used to obtain high density cell amplification by utilizing hollow fibers to create a semi-permeable barrier between the cell growth chamber and the medium flow. Since the surface area provided by this design is large, using this fiber as a culture substrate allows the production of large numbers of cells. Cells growing in the 3-dimensional environment within the bioreactor are bathed in fresh medium as it perfuses through the hollow fibers.

To replicate the topography of the intestine, Costello et al. developed a 3-D printed bioreactor that can both contain porous villus scaffolds via micromolding (Costello et al. 2017 Scientific Reports 7(12515): 1-10). This geometrically complex molded scaffold provided separation of the apical and basolateral spaces in a manner in which fluid flow exposes intestinal epithelial cells to physiologically relevant shear stresses (Costello et al. 2017). Similarly, a long-term culture in vitro culture in a simulated gut-like environment was created by Morada et al. using a hollow fiber bioreactor which allowed for two controlled separate environments (biphasic) to provide host cells with oxygen and nutrients from the basal layer, while allowing a low oxygen nutrient rich environment to be developed on the apical surface (Morada et al. 2016 International Journal for Parasitology 26: 21-29).

In configuring the hollow fiber bioreactor, there are design considerations and parameters that can be varied depending upon the goals associated with expansion of the cells. One such design consideration is the size of the pores in the fiber wall. This is generally designed to allow the passage of nutrients to the cells, carry away waste, provide desired products to the cells (such as growth factors), to remove desired products from the cells, and exclude certain factors that may be present from reaching the cells. Accordingly, the pore size of the fiber walls can be varied to modify which components will pass through the walls. For example, pore size can allow the passage of large proteinaceous molecules, including growth factors, including, but not limited to, epidermal growth factor and platelet-derived growth factor. The person of ordinary skill in the art would understand how to vary the pore size depending upon the components that it is desirable to pass through the fiber walls to reach the cells or to carry material from the cells.

In some embodiments, the pore size is about 0.2 μm. In some embodiments, the pore size is about 0.1. In some embodiments, the pore size is about 0.2 μm. In some embodiments, the pore size is about 0.3 μm. In some embodiments, the pore size is about 0.4 μm. In some embodiments, the pore size is about 0.5 μm. In some embodiments, the pore size is about 0.6 μm. In some embodiments, the pore size is about 0.7 μm. In some embodiments, the pore size is about 0.8 μm. In some embodiments, the pore size is about 0.9 μm. In some embodiments, the pore size is about 1.0 μm. In some embodiments, the pore size is about 1.1 μm. In some embodiments, the pore size is about 1.2 μm. In some embodiments, the pore size is about 1.3 μm. In some embodiments, the pore size is about 1.4 μm. In some embodiments, the pore size is about 1.5 μm. In some embodiments, the pore size is about 1.6 μm. In some embodiments, the pore size is about 1.7 μm. In some embodiments, the pore size is about 1.8 μm. In some embodiments, the pore size is about 1.9 μm. In some embodiments, the pore size is about 2.0 μm. In some embodiments, the pore size is about 2.1 μm. In some embodiments, the pore size is about 2.2 μm. In some embodiments, the pore size is about 2.2 μm. In some embodiments, the pore size is about 2.3 μm. In some embodiments, the pore size is about 2.4 μm. In some embodiments, the pore size is about 2.5 μm. In some embodiments, the pore size is about 2.6 μm. In some embodiments, the pore size is about 2.7 μm. In some embodiments, the pore size is about 2.8 μm. In some embodiments, the pore size is about 2.9 μm. In some embodiments, the pore size is about 3.0 μm.

Methods of Making Live Cell Constructs

Disclosed herein, in certain embodiments, are methods of making a live cell construct for producing a cultured milk product. In some embodiments, the method comprises (a) isolating primary mammary epithelial cells, myoepithelial cells and/or mammary progenitor cells from mammary explants from mammary tissue (e.g., breast, udder, teat tissue), biopsy sample, or raw breastmilk, to produce isolated mammary epithelial cells, myoepithelial cells and/or mammary progenitor cells; (b) culturing the isolated primary mammary epithelial cells, myoepithelial cells and/or mammary progenitor cells to produce a mixed population of primary mammary epithelial cells, mammary myoepithelial cells and mammary progenitor cells; (c) cultivating the mixed population of (b) on a scaffold having an upper surface and lower surface, to produce a polarized, monolayer of primary mammary epithelial cells, myoepithelial cells and mammary progenitor cells of the mixed population on the upper surface of the scaffold, wherein the polarized monolayer comprises an apical surface and a basal surface, thereby producing a live cell construct for producing the cultured milk product.

In some embodiments, the method comprises: a) isolating primary mammary epithelial cells, myoepithelial cells, and/or mammary progenitor cells from mammary explants from mammary tissue (e.g., breast, udder, teat tissue), biopsy sample, or raw breastmilk, to produce isolated mammary epithelial cells, myoepithelial cells, and/or mammary progenitor cells; (b) culturing the isolated primary mammary epithelial cells, myoepithelial cells, and/or mammary progenitor cells to produce a mixed population of primary mammary epithelial cells, mammary myoepithelial cells and mammary progenitor cells; (c) sorting the mixed population of primary mammary epithelial cells, myoepithelial cells, and/or mammary progenitor cells (e.g., selecting the primary mammary epithelial cells) to produce a population of primary mammary epithelial cells; and (d) cultivating the population of primary mammary epithelial on a scaffold having an upper surface and lower surface, to produce a polarized monolayer of primary mammary epithelial cells on the upper surface of the scaffold, wherein the polarized monolayer comprises an apical surface and a basal surface, thereby producing a live cell construct for producing the cultured milk product.

In some embodiments, the method comprises (a) culturing immortalized mammary epithelial cells to produce increased numbers of immortalized mammary epithelial cells; (b) cultivating the immortalized mammary epithelial cells of (a) on a scaffold, the scaffold having an upper surface and lower surface, to produce a polarized monolayer of immortalized mammary epithelial cells on the upper surface of the scaffold, wherein the polarized monolayer comprises an apical surface and a basal surface, thereby producing a live cell construct for producing the cultured milk product.

In some embodiments, the culturing and/or cultivating of the mammary cells for the live cell construct is carried out at a temperature of about 35° C. to about 39° C. (e.g., a temperature of about 35° C., 35.5° C., 36° C., 36.5° C., 37° C., 37.5° C., 38° C., 38.5° C. or about 39° C., or any value or range therein, e.g., about 35° C. to about 38° C., about 36° C. to about 39° C., about 36.5° C. to about 39° C., about 36.5° C. to about 37.5° C., or about 36.5° C. to about 38° C.). In some embodiments, the culturing and/or cultivating is carried out at a temperature of about 37° C.

In some embodiments, the culturing and/or cultivating of the mammary cells for the live cell construct is carried out at an atmospheric concentration of $CO_2$ of about 4% to about 6%, e.g., an atmospheric concentration of $CO_2$ of about 4%, 4.25%, 4.5%, 4.75%, 5%, 5.25%, 5.5%, 5.75%, or 6% or any value or range therein, e.g., about 4% to about 5.5%, about 4.5% to about 6%, about 4.5% to about 5.5%, or about 5% to about 6%). In some embodiments, the culturing and/or cultivating is carried out at an atmospheric concentration of $CO_2$ of about 5%.

In some embodiments, the culturing and/or cultivating of the mammary cells for the live cell construct comprises culturing and/or cultivating in a culture medium that is exchanged about every day to about every 10 days (e.g., every 1 day, every 2 days, every 3 days, every 4 days, every 5 days, every 6 days, every 7 days, every 8 days, every 9 days, every 10 days, or any value or range therein, e.g., about every day to every 3 days, about every 3 days to every 10 days, about every 2 days to every 5 days). In some embodiments, the culturing and/or cultivating further comprises culturing in a culture medium that is exchanged about every day to about every few hours to about every 10 days, e.g., about every 1, 2, 3, 4, 5, 6, 7, 8, 9, 10, 11, 12, 13, 14, 15, 16, 17, 18, 19, 20, 21, 22, 23, or 24 hours to about every 1, 2, 3, 4, 5, 6, 7, 8, 9, or 10 days or any value or range therein. For example, in some embodiments, the culturing and/or cultivating further comprises culturing and/or cultivating in a culture medium that is exchanged about every 12 hours to about every 10 days, about every 10 hours to about every 5 days, or about every 5 hours to about every 3 days.

In some embodiments, the live cell construct is stored in a freezer or in liquid nitrogen. The storage temperature depends on the desired storage length. For example, freezer temperature (e.g., storage at a temperature of about 0° C. to about −80° C. or less, e.g., about 0° C., −10° C., −20° C., −30° C., −40° C., −50° C., −60° C., −70° C., −80° C., −90° C., −100° C. or any value or range therein) may be used if the cells are to be used within 6 months (e.g., within 1, 2, 3, 4, 5, or 6 months). For example, liquid nitrogen may be used (e.g., storage at a temperature of −100° C. or less (e.g., about −100° C., −110° C., −120° C., −130, −140, −150, −160, −170, −180, −190° C., −200° C., or less) for longer term storage (e.g., storage of 6 months or longer, e.g., 6, 7, 8, 9, 10, 11, or 12 months, or 1, 2, 3, 4, 5, 6 or more years).

In some embodiments, the mammary cells are isolated and sorted via fluorescence-activated cell sorting, magnetic-activated cell sorting, and/or microfluidic cell sorting.

Basal Culture Media and Lactogenic Media

In some embodiments, the culture medium comprises a carbon source, a chemical buffering system, one or more essential amino acids, one or more vitamins and/or cofactors, and one or more inorganic salts. In some embodiments, the carbon source, chemical buffering system, one or more essential amino acids, one or more vitamins and/or cofactors, and/or one or more inorganic salts are food grade.

In some embodiments, the culture medium is lactogenic culture medium. In some embodiments, the culture medium further comprises prolactin (e.g., mammalian prolactin, e.g., human prolactin), linoleic and alpha-linoleic acid, estrogen and/or progesterone. For example, in some embodiments, the culture medium comprises prolactin (or prolactin is added) in an amount from about 20 ng/mL to about 200 ng/L of culture medium, e.g., about 20, 30, 40, 50, 60, 70, 80, 90, 100, 110, 120, 130, 140, 150, 160, 170, 180, 190, or 200 ng/mL or any value or range therein. In some embodiments, the culture medium comprises prolactin (or prolactin is added) in an amount from about 20 ng/mL to about 195 ng/mL, about 50 ng/mL to about 150 ng/mL, about 25 ng/mL to about 175 ng/mL, about 45 ng/mL to about 200 ng/mL, or about 75 ng/mL to about 190 ng/mL of culture medium. In some embodiments, the culture medium further comprises other factors to improve efficiency, including, but not limited to, insulin, an epidermal growth factor, and/or a hydrocortisone.

In some embodiments, the culture medium comprises a carbon source in an amount from about 1 g/L to about 15 g/L of culture medium (e.g., about 1, 2, 3, 4, 5, 6, 7, 8, 9, 10, 11, 12, 13, 14 or 15 g/L or any value or range therein), or about 1, 2, 3, 4, 5 or 6 g/L to about 7, 8, 9, or 10, 11, 12, 13, 14 or 15 g/L of the culture medium. Non-limiting examples of a carbon source include glucose and/or pyruvate. For example, in some embodiments, the culture medium comprises glucose in an amount from about 1g/L to about 12 g/L of culture medium, e.g., about 1, 2, 3, 4, 5, 6, 7, 8, 9, 10, 11, or 12 g/L or any value or range therein. In some embodiments, the culture medium comprises glucose in an amount from about 1 g/L to about 6 g/L, about 4 g/L to about 12 g/L, about 2.5 g/L to about 10.5 g/L, about 1.5 g/L to about 11.5 g/L, or about 2 g/L to about 10 g/L of culture medium. In some embodiments, the culture medium comprises glucose in an amount from about 1, 2, 3, or 4 g/L to about 5, 6, 7, 8, 9, 10, 11, or 12 g/L or about 1, 2, 3, 4, 5, or 6 g/L to about 7, 8, 9, 10, 11, or 12 g/L. In some embodiments, the culture medium comprises pyruvate in an amount from about 5 g/L to about 15 g/L of culture medium, e.g., about 5, 6, 7, 8, 9, 10, 11, 12, 13, 14, or 15 g/L or any value or range therein. In some embodiments, the culture medium comprises pyruvate in an amount from about 5 g/L to about 14.5 g/L, about 10 g/L to about 15 g/L, about 7.5 g/L to about 10.5 g/L, about 5.5 g/L to about 14.5 g/L, or about 8 g/L to about 10 g/L of culture medium. In some embodiments, the culture medium comprises pyruvate in an amount from about 5, 6, 7, or 8 g/L to about 9, 10, 11, 12, 13, 14 or 15 g/L or about 5, 6, 7, 8, 9, or 10 g/L to about 11, 12, 13, 14 or 15 g/L.

In some embodiments, the culture medium comprises a chemical buffering system in an amount from about 1 g/L to about 4 g/L (e.g., about 1, 1.5, 2, 2.5, 3, 3.5, or 4 g/L or any value or range therein) of culture medium or about 10 mM to about 25 mM (e.g., about 10, 11, 12, 13, 14, 15, 16, 17, 18, 19, 20, 21, 22, 23, 24, or 25 mM or any value or range therein). In some embodiments, the chemical buffering system includes, but is not limited to, sodium bicarbonate and/or 4-(2-hydroxyethyl)-1-piperazineethanesulfonic acid (HEPES). For example, in some embodiments, the culture medium comprises sodium bicarbonate in an amount from about 1 g/L to about 4 g/L of culture medium, e.g., about 1, 1.5, 2, 2.5, 3, 3.5, or 4 g/L or any value or range therein. In some embodiments, the culture medium comprises sodium bicarbonate in an amount from about 1 g/L to about 3.75 g/L, about 1.25 g/L to about 4 g/L, about 2.5 g/L to about 3 g/L, about 1.5 g/L to about 4 g/L, or about 2 g/L to about 3.5 g/L of culture medium. In some embodiments, the culture medium comprises HEPES in an amount from about 10 mM to about 25 mM, e.g., about 10, 11, 12, 13, 14, 15, 16, 17, 18, 19, 20, 21, 22, 23, 24, or 25 mM or any value or range therein. In some embodiments, the culture medium comprises HEPES in an amount from about 11 mM to about 25 mM, about 10 mM to about 20 mM, about 12.5 mM to about 22.5 mM, about 15 mM to about 20.75 mM, or about 10 mM to about 20 mM.

In some embodiments, the culture medium comprises one or more essential amino acids in an amount from about 0.5 mM to about 5 mM (e.g., about 0.5, 1, 1.5, 2, 2.5, 3, 3.5, 4, 4.5, or 5 mM or any value or range therein) or about 0.5, 1, 1.5, 2 mM to about 2.5, 3, 3.5, 4, 4.5, or 5 mM. In some embodiments, the one or more essential amino acids is histidine, isoleucine, leucine, lysine, methionine, phenylalanine, threonine, tryptophan, valine, and/or arginine. For example, in some embodiments, the culture medium comprises arginine in an amount from about 0.5 mM to about 5 mM, e.g., about 0.5, 1, 1.5, 2, 2.5, 3, 3.5, 4, 4.5, or 5 mM or any value or range therein. In some embodiments, the culture medium comprises an essential amino acids in an amount from about 0.5 mM to about 4.75 mM, about 2 mM to about 3.5 mM, about 0.5 mM to about 3.5 mM, about 1 mM to about 5 mM, or about 3.5 mM to about 5 mM.

In some embodiments, the culture medium comprises one or more vitamins and/or cofactors in an amount from about 0.01 μM to about 50 μM (e.g., about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 3, 4, 5, 6, 7, 8, 9, 10, 12.5, 15, 17.5, 20, 25, 30, 35, 40, 45, 46, 47, 48, 49, 49.025, 49.05, 49.075, or 50 μM or any value or range therein) or about 0.01, 0.02, 0.03, 0.04, 0.05, 0.06, 0.07, 0.08, 0.09, 0.1, 0.2, 0.3, 0.4, 0.5, 0.6, 0.7, 0.8, or 0.9 μM to about 1, 1.1, 1.2, 1.3, 1.4, 1.5, 1.6, 1.7, 1.8, 1.9, 2, 2.1, 2.2, 2.3, 2.4, 2.5, 3, 4, 5, 6 μM or about 0.02, 0.025, 0.05, 0.075, 1, 1.5, 2, 3, 4, 5, 6, 7, 8, 9, 10 μM to about 12.5, 15, 17.5, 20, 25, 30, 35, 40, 45, 46, 47, 48, 49, 49.025, 49.05, 49.075, or 50 μM. In some embodiments, one or more vitamins and/or cofactors include, but are not limited to, thiamine and/or riboflavin. For example, in some embodiments, the culture medium comprises thiamine in an amount from about 0.025 μM to about 50 μM, e.g., about 0.025, 0.05, 0.075, 1, 1.5, 2, 3, 4, 5, 6, 7, 8, 9, 10, 12.5, 15, 17.5, 20, 25, 30, 35, 40, 45, 46, 47, 48, 49, 49.025, 49.05, 49.075, or 50 μM or any value or range therein. In some embodiments, the culture medium comprises thiamine in an amount from about 0.025 μM to about 45.075 μM, about 1 μM to about 40 µM, about 5 µM to about 35.075 µM, about 10 µM to about 50 µM, or about 0.05 µM to about 45.5 µM. In some embodiments, the culture medium comprises riboflavin in an amount from about 0.01 µM to about 3 µM, e.g., about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 µM or any value or range therein. In some embodiments, the culture medium comprises riboflavin in an amount from about 0.01 µM to about 2.05 µM, about 1 µM to about 2.95 µM, about 0.05 µM to about 3 µM, about 0.08 µM to about 1.55 µM, or about 0.05 µM to about 2.9 µM.

In some embodiments, the culture medium comprises one or more inorganic salts in an amount from about 100 mg/L to about 150 mg/L of culture medium (e.g., about 100, 105, 110, 115, 120, 125, 130, 135, 140, 145, or 150 mg/L or any value or range therein) or about 100 mg/L to about 150 mg/L of culture medium (e.g., about 100, 105, 110, 115, 120, 125, 130, 135, 140, 145, or 150 mg/L or any value or range therein). In some embodiments, one or more inorganic salts include, but are not limited to, calcium and/or magnesium. For example, in some embodiments, the culture medium comprises calcium in an amount from about 100 mg/L to about 150 mg/L of culture medium, e.g., about 100, 105, 110, 115, 120, 125, 130, 135, 140, 145, or 150 mg/L or any value or range therein. In some embodiments, the culture medium comprises arginine in an amount from about 100 mg/L to about 125 mg/L, about 105 mg/L to about 150 mg/L, about 120 mg/L to about 130 mg/L, or about 100 mg/L to about 145 mg/L of culture medium. In some embodiments, the culture medium comprises magnesium in an amount from about 0.01 mM to about 1 mM, e.g., about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 0.91, 0.92, 0.93, 0.94, 0.95, 0.96, 0.97, 0.98, 0.99, or 1 mM or any value or range therein. In some embodiments, the culture medium comprises magnesium in an amount from about 0.05 mM to about 1 mM, about 0.01 mM to about 0.78 mM, about 0.5 mM to about 1 mM, about 0.03 mM to about 0.75 mM, or about 0.25 mM to about 0.95 mM.

In some embodiments, the culture medium comprises a carbon source in an amount from about 1 g/L to about 15 g/L of culture medium (e.g., about 1, 2, 3, 4, 5, 6, 7, 8, 9, 10, 11, 12, 13, 14 or 15 g/L or any value or range therein), or about 1, 2, 3, 4, 5 or 6 g/L to about 7, 8, 9, or 10, 11, 12, 13, 14 or 15 g/L of the culture medium. In some embodiments, the carbon source includes, but is not limited to, glucose and/or pyruvate. For example, in some embodiments, the culture medium comprises glucose in an amount from about 1 g/L to about 12 g/L of culture medium, e.g., about 1, 2, 3, 4, 5, 6, 7, 8, 9, 10, 11, or 12 g/L or any value or range therein. In some embodiments, the culture medium comprises glucose in an amount from about 1 g/L to about 6 g/L, about 4 g/L to about 12 g/L, about 2.5 g/L to about 10.5 g/L, about 1.5 g/L to about 11.5 g/L, or about 2 g/L to about 10 g/L of culture medium. In some embodiments, the culture medium comprises pyruvate at an amount of about 5 g/L to about 15 g/L of culture medium, e.g., about 5, 6, 7, 8, 9, 10, 11, 12, 13, 14, or 15 g/L or any value or range therein. In some embodiments, the culture medium comprises pyruvate in an amount from about 5 g/L to about 14.5 g/L, about 10 g/L to about 15 g/L, about 7.5 g/L to about 10.5 g/L, about 5.5 g/L to about 14.5 g/L, or about 8 g/L to about 10 g/L of culture medium.

In some embodiments, the culture medium comprises a chemical buffering system in an amount from about 1 g/L to about 4 g/L (e.g., about 1, 1.5, 2, 2.5, 3, 3.5, or 4 g/L or any value or range therein) of culture medium or about 10 mM to about 25 mM (e.g., about 10, 11, 12, 13, 14, 15, 16, 17, 18, 19, 20, 21, 22, 23, 24, or 25 mM or any value or range therein). In some embodiments, the chemical buffering system includes, but is not limited to, sodium bicarbonate and/or HEPES. For example, in some embodiments, the culture medium comprises sodium bicarbonate in an amount from about 1 g/L to about 4 g/L of culture medium, e.g., about 1, 1.5, 2, 2.5, 3, 3.5, or 4 g/L or any value or range therein. In some embodiments, the culture medium comprises sodium bicarbonate in an amount from about 1 g/L to about 3.75 g/L, about 1.25 g/L to about 4 g/L, about 2.5 g/L to about 3 g/L, about 1.5 g/L to about 4 g/L, or about 2 g/L to about 3.5 g/L of culture medium. In some embodiments, the culture medium comprises HEPES in an amount from about 10 mM to about 25 mM, e.g., about 10, 11, 12, 13, 14, 15, 16, 17, 18, 19, 20, 21, 22, 23, 24, or 25 mM or any value or range therein. In some embodiments, the culture medium comprises HEPES in an amount from about 1 mM to about 25 mM, about 10 mM to about 20 mM, about 12.5 mM to about 22.5 mM, about 15 mM to about 20.75 mM, or about 10 mM to about 20 mM.

In some embodiments, the culture medium comprises one or more essential amino acids in an amount from about 0.5 mM to about 5 mM (e.g., about 0.5, 1, 1.5, 2, 2.5, 3, 3.5, 4, 4.5, or 5 mM or any value or range therein) or about 0.5, 1, 1.5, 2 mM to about 2.5, 3, 3.5, 4, 4.5, or 5 mM. In some embodiments, one or more essential amino acids is arginine and/or cysteine. For example, in some embodiments, the culture medium comprises arginine in an amount from about 0.5 mM to about 5 mM, e.g., about 0.5, 1, 1.5, 2, 2.5, 3, 3.5, 4, 4.5, or 5 mM or any value or range therein. In some embodiments, the culture medium comprises arginine in an amount from about 0.5 mM to about 4.75 mM, about 2 mM to about 3.5 mM, about 0.5 mM to about 3.5 mM, about 1 mM to about 5 mM, or about 3.5 mM to about 5 mM. For example, in some embodiments, the culture medium comprises cysteine in an amount from about 0.5 mM to about 5 mM, e.g., about 0.5, 1, 1.5, 2, 2.5, 3, 3.5, 4, 4.5, or 5 mM or any value or range therein. In some embodiments, the culture medium comprises cysteine in an amount from about 0.5 mM to about 4.75 mM, about 2 mM to about 3.5 mM, about 0.5 mM to about 3.5 mM, about 1 mM to about 5 mM, or about 3.5 mM to about 5 mM.

In some embodiments, the culture medium comprises one or more vitamins and/or cofactors in an amount from about 0.01 µM to about 50 µM (e.g., about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 3, 4, 5, 6, 7, 8, 9, 10, 12.5, 15, 17.5, 20, 25, 30, 35, 40, 45, 46, 47, 48, 49, 49.025, 49.05, 49.075, or 50 µM or any value or range therein) or about 0.01, 0.02, 0.03, 0.04, 0.05, 0.06, 0.07, 0.08, 0.09, 0.1, 0.2, 0.3, 0.4, 0.5, 0.6, 0.7, 0.8, or 0.9 µM to about 1, 1.1, 1.2, 1.3, 1.4, 1.5, 1.6, 1.7, 1.8, 1.9, 2, 2.1, 2.2, 2.3, 2.4, 2.5, 3, 4, 5, 6 µM or about 0.02, 0.025, 0.05, 0.075, 1, 1.5, 2, 3, 4, 5, 6, 7, 8, 9, 10 µM to about 12.5, 15, 17.5, 20, 25, 30, 35, 40, 45, 46, 47, 48, 49, 49.025, 49.05, 49.075, or 50 µM. In some embodiments, one or more vitamins and/or cofactors includes, but is not limited to, thiamine and/or riboflavin. For example, in some embodiments, the culture medium comprises thiamine in an amount from about 0.025 µM to about 50 µM, e.g., 0.025, 0.05, 0.075, 1, 1.5, 2, 3, 4, 5, 6, 7, 8, 9, 10, 12.5, 15, 17.5, 20, 25, 30, 35, 40, 45, 46, 47, 48, 49, 49.025, 49.05, 49.075, or 50 µM or any value or range therein. In some embodiments, the culture medium comprises thiamine in an amount from about 0.025 µM to about 45.075 µM, about 1 µM to about 40 µM, about 5 µM to about 35.075 µM, about 10 µM to about 50 µM, or about 0.05 µM to about 45.5 µM. In some embodiments, the culture medium comprises riboflavin in an amount from about 0.01 µM to about 3 µM, e.g., 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 µM or any value or range therein. In some embodiments, the culture medium comprises riboflavin in an amount from about 0.01 µM to about 2.05 µM, about 1 µM to about 2.95 µM, about 0.05 µM to about 3 µM, about 0.08 µM to about 1.55 µM, or about 0.05 µM to about 2.9 µM.

In some embodiments, the culture medium comprises one or more inorganic salts in an amount from about 100 mg/L to about 150 mg/L of culture medium (e.g., about 100, 105, 110, 115, 120, 125, 130, 135, 140, 145, or 150 mg/L or any value or range therein) or about 100 mg/L to about 150 mg/L of culture medium (e.g., about 100, 105, 110, 115, 120, 125, 130, 135, 140, 145, or 150 mg/L or any value or range therein). In some embodiments, exemplary one or more inorganic salts is calcium and/or magnesium. For example, in some embodiments, the culture medium comprises calcium in an amount from about 100 mg/L to about 150 mg/L of culture medium, e.g., about 100, 105, 110, 115, 120, 125, 130, 135, 140, 145, or 150 mg/L or any value or range therein. In some embodiments, the culture medium comprises arginine in an amount from about 100 mg/L to about 125 mg/L, about 105 mg/L to about 150 mg/L, about 120 mg/L to about 130 mg/L, or about 100 mg/L to about 145 mg/L of culture medium. In some embodiments, the culture medium comprises magnesium in an amount from about 0.01 mM to about 1 mM, e.g., about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 0.91, 0.92, 0.93, 0.94, 0.95, 0.96, 0.97, 0.98, 0.99, or 1 mM or any value or range therein. In some embodiments, the culture medium comprises magnesium in an amount from about 0.05 mM to about 1 mM, about 0.01 mM to about 0.78 mM, about 0.5 mM to about 1 mM, about 0.03 mM to about 0.75 mM, or about 0.25 mM to about 0.95 mM.

In some embodiments, the carbon source, chemical buffering system, one or more essential amino acids, one or more vitamins and/or cofactors, and/or one or more inorganic salts is food grade.

In some embodiments, the culture medium is lactogenic culture medium, e.g., the culture medium further comprises prolactin (e.g., mammalian prolactin, e.g., human prolactin). For example, in some embodiments, the culture medium comprises prolactin (or prolactin is added) in an amount from about 20 ng/mL to about 200 ng/L of culture medium, e.g., about 20, 30, 40, 50, 60, 70, 80, 90, 100, 110, 120, 130, 140, 150, 160, 170, 180, 190, or 200 ng/mL or any value or range therein. In some embodiments, the culture medium comprises prolactin (or prolactin is added) in an amount from about 20 ng/mL to about 195 ng/mL, about 50 ng/mL to about 150 ng/mL, about 25 ng/mL to about 175 ng/mL, about 45 ng/mL to about 200 ng/mL, or about 75 ng/mL to about 190 ng/mL of culture medium. In some embodiments, the methods further comprise adding prolactin to the culture medium, thereby providing a lactogenic culture medium. In some embodiments, the prolactin is produced by a microbial cell and/or a human cell expressing a recombinant prolactin (e.g., a prolactin comprising a substitution of a serine residue at position 179 of the prolactin gene with aspartate (S179D), e.g., S179D-prolactin). In some embodiments, adding prolactin to the culture medium comprises conditioning culture medium by culturing cells that express and secrete prolactin, and applying the conditioned culture medium comprising prolactin to the basal surface of the monolayer of primary mammary epithelial cells, the basal surface of the monolayer of the mixed population, or the basal surface of the monolayer of live immortalized mammary epithelial cells.

In some embodiments, the culture medium further comprises other factors to improve efficiency, including, but not limited to, insulin, an epidermal growth factor, and/or a hydrocortisone. In some embodiments, the methods of the present invention further comprise adding other factors (e.g., insulin, an epidermal growth factor, and/or a hydrocortisone) to the culture medium, e.g., to improve efficiency.

Methods of Producing Cultured Milk Products

Disclosed herein, in certain embodiments, are methods of making a cultured milk product. In some embodiments, the method comprises culturing a live cell construct disclosed herein in a bioreactor comprising a basal compartment and an apical compartment, wherein the basal compartment comprises a culture media and the mammary cells secret the cultured milk product into the apical compartment.

In some embodiments, the live cell construct comprises a scaffold comprising an upper surface and a lower surface and a polarized monolayer of live primary mammary epithelial cells, a continuous polarized monolayer of a mixed population of live primary mammary epithelial cells, mammary myoepithelial cells and mammary progenitor cells, and/or a continuous polarized monolayer of live immortalized mammary epithelial cells having an apical surface and a basal surface, wherein the continuous polarized monolayer of live primary mammary epithelial cells, the continuous polarized monolayer of the mixed population of live primary mammary epithelial cells, mammary myoepithelial cells and mammary progenitor cells and/or the continuous polarized monolayer of live immortalized mammary epithelial cells are located on the upper surface of scaffold In some embodiments, the lower surface of the scaffold is adjacent to the basal compartment. In some embodiments, the apical surface of the continuous polarized monolayer of live primary mammary epithelial cells, the continuous polarized monolayer of the mixed population of live primary mammary epithelial cells, mammary myoepithelial cells and mammary progenitor cells, and/or the continuous polarized monolayer of live immortalized mammary epithelial cells is adjacent to the apical compartment. In some embodiments, the continuous polarized monolayer of live primary epithelial mammary cells, the live primary epithelial mammary cells of the continuous polarized monolayer of the mixed population of live primary mammary epithelial cells, mammary myoepithelial cells and mammary progenitor cells, or the continuous polarized monolayer of immortalized mammary epithelial cells secretes milk through its apical surface into the apical compartment, thereby producing milk in culture.

In some embodiments, the polarized monolayer of epithelial mammary cells forms a barrier that divides the apical compartment and the basal compartment, wherein the basal surface of the mammary cells are attached to the scaffold and the apical surface is oriented toward the apical compartment.

In some embodiments, the basal compartment is adjacent to the lower surface of the scaffold. In some embodiments, the basal compartment comprises a culture medium in fluidic contact with the basal surface of the polarized monolayer of mammary epithelial cells (e.g., the polarized monolayer of primary mammary epithelial cells, the polarized the monolayer of the mixed population, or the polarized monolayer of live immortalized mammary epithelial cells).

In some embodiments, the culture medium comprises a carbon source, a chemical buffering system, one or more essential amino acids, one or more vitamins and/or cofactors, and one or more inorganic salts.

In some embodiments, the bioreactor comprises an apical compartment that is adjacent to the apical surface of the monolayer. In some embodiments, the apical compartment is adjacent to the upper surface of the scaffold.

In some embodiments, the total cell density of mammary cells in the bioreactor is at least $10^{11}$ mammary cells. In some embodiments, the total cell density of mammary cells in the bioreactor is at least $10^{12}$ mammary cells. In some embodiments, the total cell density of mammary cells in the bioreactor is at least $10^{13}$ mammary cells.

In some embodiments, the total cell density of mammary cells in the bioreactor is about 20 to 55 cells per 100 $\mu m^2$. In some embodiments, the total cell density of mammary cells in the bioreactor is about 20 cells per 100 $\mu m^2$ In some embodiments the total cell density of mammary cells in the bioreactor is 25 cells per 100 $\mu m^2$. In some embodiments, the total cell density of mammary cells in the bioreactor is about 30 cells per 100 $\mu m^2$. In some embodiments, the total cell density of mammary cells in the bioreactor is about 35 cells per 100 $\mu m^2$. In some embodiments, the total cell density of mammary cells in the bioreactor is about 40 cells per 100 $\mu m^2$. In some embodiments, the total cell density of mammary cells in the bioreactor is about 45 cells per 100 $\mu m^2$. In some embodiments, the total cell density of mammary cells in the bioreactor is about 50 cells per 100 $\mu m^2$. In some embodiments, the total cell density of mammary cells in the bioreactor is about 55 cells per 100 $\mu m^2$.

In some embodiments, the total surface area of mammary cells within the bioreactor is at least about 1.5 $m^2$. In some embodiments, the total surface area of mammary cells within the bioreactor is at least about 2 $m^2$. In some embodiments, the total surface area of mammary cells within the bioreactor is at least about 2.5 $m^2$. In some embodiments, the total surface area of mammary cells within the bioreactor is at least about 3 $m^2$. In some embodiments, the total surface area of mammary cells within the bioreactor is at least about 4 $m^2$. In some embodiments, the total surface area of mammary cells within the bioreactor is at least about 5 $m^2$. In some embodiments, the total surface area of mammary cells within the bioreactor is at least about 10 $m^2$. In some embodiments, the total surface area of mammary cells within the bioreactor is at least about 15 $m^2$. In some embodiments, the total surface area of mammary cells within the bioreactor is at least about 20 $m^2$. In some embodiments, the total surface area of mammary cells within the bioreactor is at least about 25 $m^2$. In some embodiments, the total surface area of mammary cells within the bioreactor is at least about 50 $m^2$. In some embodiments, the total surface area of mammary cells within the bioreactor is at least about 100 $m^2$. In some embodiments, the total surface area of mammary cells within the bioreactor is at least about 250 $m^2$. In some embodiments, the total surface area of mammary cells within the bioreactor is at least about 500 $m^2$.

In some embodiments, the bioreactor maintains a temperature of about 27° C. to about 39° C. (e.g., a temperature of about 27° C., 28° C., 29° C., 30° C., 31° C., 32° C., 33° C., 34° C., 35° C., 35° C., 35.5° C., 36° C., 36.5° C., 37° C., 37.5° C., 38° C., 38.5° C. or about 39° C., or any value or range therein, e.g., about 27° C. to about 38° C., about 36° C. to about 39° C., about 36.5° C. to about 39° C., about 36.5° C. to about 37.5° C., or about 36.5° C. to about 38° C.). In some embodiments, the bioreactor maintains a temperature of about 37° C.

In some embodiments, the bioreactor has an atmospheric concentration of $CO_2$ of about 4% to about 6%, e.g., an atmospheric concentration of $CO_2$ of about 4%, 4.25%, 4.5%, 4.75%, 5%, 5.25%, 5.5%, 5.75%, or 6% or any value or range therein, e.g., about 4% to about 5.5%, about 4.5% to about 6%, about 4.5% to about 5.5%, or about 5% to about 6%). In some embodiments, the bioreactor has an atmospheric concentration of $CO_2$ of about 5%.

In some embodiments, the bioreactor has an atmospheric concentration of $CO_2$ of about 4% to about 6%, e.g., an atmospheric concentration of $CO_2$ of about 4%, 4.25%, 4.5%, 4.75%, 5%, 5.25%, 5.5%, 5.75%, or 6% or any value or range therein, e.g., about 4% to about 5.5%, about 4.5% to about 6%, about 4.5% to about 5.5%, or about 5% to about 6%). In some embodiments, the bioreactor has an atmospheric concentration of $CO_2$ of about 5%.

In some embodiments, the method comprises monitoring the concentration of dissolved $O_2$ and $CO_2$. In some embodiments, the concentration of dissolved $O2$ is maintained between about 10% to about 25% or any value or range therein (e.g., about 10, 11, 12, 13, 14, 15, 16, 17, 18, 19, 20, 21, 22, 23, 24, or 25%). For example, in some embodiments, the concentration of dissolved $O2$ is maintained between about 12% to about 25%, about 15% to about 22%, about 10% to about 20%, about 15%, about 20%, or about 22%. In some embodiments, the concentration of $CO_2$ is maintained between about 4% to about 6%, e.g., a concentration of $CO_2$ of about 4%, 4.25%, 4.5%, 4.75%, 5%, 5.25%, 5.5%, 5.75%, or 6% or any value or range therein, e.g., about 4% to about 5.5%, about 4.5% to about 6%, about 4.5% to about 5.5%, or about 5% to about 6%). In some embodiments, the concentration of $CO_2$ is maintained at about 5%.

In some embodiments, the culture medium is exchanged about every day to about every 10 days (e.g., every 1 day, every 2 days, every 3 days, every 4 days, every 5 days, every 6 days, every 7 days, every 8 days, every 9 days, every 10 days, or any value or range therein, e.g., about every day to every 3 days, about every 3 days to every 10 days, about every 2 days to every 5 days). In some embodiments, the culture medium is exchanged about every day to about every few hours to about every 10 days, e.g., about every 1, 2, 3, 4, 5, 6, 7, 8, 9, 10, 11, 12, 13, 14, 15, 16, 17, 18, 19, 20, 21, 22, 23, or 24 hours to about every 1, 2, 3, 4, 5, 6, 7, 8, 9, or 10 days or any value or range therein. For example, in some embodiments, the culture medium is exchanged about every 12 hours to about every 10 days, about every 10 hours to about every 5 days, or about every 5 hours to about every 3 days.

In some embodiments, the method comprises monitoring the glucose concentration and/or rate of glucose consumption in the culture medium and/or in the lactogenic culture medium. In some embodiments, the prolactin is added when the rate of glucose consumption in the culture medium is steady state.

In some embodiments, the method further comprises applying transepithelial electrical resistance (TEER) to measure the maintenance of the monolayer of epithelial cells. TEER measures a voltage difference between the fluids (e.g., media) in two compartments (e.g., between the apical and basal compartments), wherein if the barrier between the compartments loses integrity, the fluids in the two compartments may mix. When there is fluid mixing, the voltage difference will be reduced or eliminated; a voltage difference indicates that the barrier is intact. In some embodiments, upon detection of a loss of voltage by TEER, a scaffold (e.g., a Transwell® filter, a microstructured bioreactor, a decellularized tissue, a hollow fiber bioreactor, etc.) is reinoculated with additional cells and allowed time to reestablish a barrier (e.g., a monolayer) before resuming production of the cultured milk product (e.g., milk production).

In some embodiments, the method further comprises collecting the cultured milk product from the apical compartment to produce collected cultured milk product. In some embodiments, the collecting is via a port, via gravity, and/or via a vacuum. In some embodiments, a vacuum is attached to a port.

In some embodiments, the method further comprises freezing the collected cultured milk product to produce frozen cultured milk product and/or lyophilizing the collected cultured milk product to produce lyophilized cultured milk product.

In some embodiments, the method further comprises packaging the collected cultured milk product, the frozen cultured milk product and/or the lyophilized cultured milk product into a container.

In some embodiments, the method further comprises extracting one or more components from the collected cultured milk product. Non-limiting examples of components from the collected cultured milk product include milk protein, lipid, carbohydrate, vitamin, and/or mineral contents. In some embodiments, the components from the collected cultured milk product are lyophilized and/or concentrated to produce a lyophilized or a concentrated cultured milk product component product. In some embodiments, the components from the collected cultured milk product are concentrated by, e.g., membrane filtration and/or reverse osmosis. In some embodiments, the lyophilized or concentrated cultured milk product component product is packaged in a container, optionally wherein the container is sterile and/or a food grade container. In some embodiments, the container is vacuum-sealed. In some embodiments, the container is a canister, a jar, a bottle, a bag, a box, or a pouch.

Cultured Milk Products

Disclosed herein, in certain embodiments, are cultured milk products. In some embodiments, the cultured milk product is a standardized, sterile cultured milk product. In some embodiments, the cultured milk product is for nutritional use.

In some embodiments, the cultured milk product is produced by any method disclosed herein.

Breast milk contains low but measurable concentrations of environmental contaminants, health-harming chemicals from industry and manufacturing products that are widely spread in the environment. Environmental contaminants are partly secreted in breast milk. The contaminant levels in breast milk reflect those in the mother's body and are therefore ideal for monitoring exposure levels. Toxic environmental contaminants can be transferred from mother to infant via breastfeeding. Persistent organic pollutants (POPs) are a family of lipophilic stable chemicals that bioaccumulate in adipose tissue and create a lasting toxic body burden. Breastfeeding provides a significant source of exposure to POPs early in human life, the effects of which are unknown.

In some embodiments, the cultured milk product does not comprise or is substantially free of one or more environmental contaminants. In some embodiments, the cultured milk product does not comprise or is substantially free of persistent organic pollutants (POPs). In some embodiments, the cultured milk product does not comprise or is substantially free of polychlorinated dibenzo-p-dioxins (PCDDs), polychlorinated dibenzofurans (PCDFs), polychlorinated biphenyls (PCBs) and pesticides such as DDT.

Heavy metals such as mercury, lead, arsenic, cadmium, nickel, chromium, cobalt, zinc, and other potentially toxic metals that are dispersed throughout the environment also have bioaccumulative features known to accumulate in human milk and thus are of concern to the nursing infant. Metal in breast milk originates from exogenous sources, i.e., uptake via contaminated air, food, and drinking water, and endogenous release along with essential trace elements. For example, lead and mercury are equally dispersed in the human food chain, and their impact on fetal development is heavily determined by the mother's diet and nutritional status. The exposures to toxic metals have significant public health implication, even at small concentrations and acute exposures, these metals remain toxic to humans. A nursing infant may be exposed to toxic metals in a period of highest susceptibility. Nursing infants may be exposed to heavy metals through breast milk in excess of what they should, and exposure may have health implication for the infants. For infants in particular, these exposures may have adverse effect on the developing central nervous system, leaving a life-long defect on their cognitive abilities.

In some embodiments, the cultured milk product does not comprise or is substantially free of one or more heavy metals, such as arsenic, lead, cadmium, nickel, mercury, chromium, cobalt, and zinc. In some embodiments, the cultured milk product does not comprise or is substantially free of arsenic. In some embodiments, the cultured milk product does not comprise or is substantially free of lead. In some embodiments, the cultured milk product does not comprise or is substantially free of cadmium. In some embodiments, the cultured milk product does not comprise or is substantially free of nickel. In some embodiments, the cultured milk product does not comprise or is substantially free of mercury. In some embodiments, the cultured milk product does not comprise or is substantially free of chromium. In some embodiments, the cultured milk product does not comprise or is substantially free of cobalt. In some embodiments, the cultured milk product does not comprise or is substantially free of zinc. In some embodiments, the cultured milk product does not comprise or is substantially free of arsenic, lead, cadmium, nickel, mercury, chromium, cobalt, and zinc.

Foreign allergenic proteins can be difficult to distinguish from endogenous human milk proteins. Food proteins with allergenic potential that have been detected in human milk include hen's egg and peanut proteins. There are eight major food allergens, known as the big 8, that are responsible for most of the serious food allergy reactions in the U.S. The big 8 list is comprised of milk, egg, fish, crustacean shellfish, tree nuts, peanuts, wheat, and soybean allergens. Proteins known to cause egg allergy include ovomucoid, ovalbumin, and conalbumin. Peanuts proteins include arachin 6, arachin 3, conarachin, main allergen Arah1, and arachin Arah2. As an example of maternal dietary protein transportation to milk, it has been shown that the consumption of one egg per day leads to higher concentrations of the chicken egg allergen ovalbumin (OVA) in human milk compared to egg-avoiding mothers.

In some embodiments, the cultured milk product does not comprise or is substantially free of one or more food allergens. In some embodiments, the cultured milk product does not comprise or is substantially free of egg, fish, crustacean shellfish, tree nuts, peanuts, wheat, and soybean allergens. In some embodiments, the cultured milk product does not comprise or is substantially free of egg allergens. In some embodiments, the cultured milk product does not comprise or is substantially free of fish allergens. In some embodiments, the cultured milk product does not comprise or is substantially free of crustacean allergens. In some embodiments, the cultured milk product does not comprise or is substantially free of tree nut allergens. In some embodiments, the cultured milk product does not comprise or is substantially free of peanut allergens. In some embodiments, the cultured milk product does not comprise or is substantially free of wheat allergens. In some embodiments, the cultured milk product does not comprise or is substantially free of soybean allergens.

In some embodiments, the cultured milk product does not comprise or is substantially free of arachin 6, arachin 3, conarachin, Arah1, and Arah2.

In some embodiments, the cultured milk product does not comprise or is substantially free of ovalbumin (OVA).

Having described the present invention, the same will be explained in greater detail in the following examples, which are included herein for illustration purposes only, and which are not intended to be limiting to the invention.

EXAMPLES

Example 1

A cell culture system designed for the collection of milk should support compartmentalized secretion of the product such that the milk is not exposed to the media that provides nutrients to the cells. In the body, milk-producing epithelial cells line the interior surface of the mammary gland as a continuous monolayer. The monolayer is oriented such that the basal surface is attached to an underlying basement membrane, while milk is secreted from the apical surface and stored in the luminal compartment of the gland, or alveolus, until it is removed during milking or feeding. Tight junctions along the lateral surfaces of the cells ensure a barrier between the underlying tissues and the milk located in the alveolar compartment. Therefore, in vivo, the tissue of the mammary gland is arranged such that milk secretion is compartmentalized, with the mammary epithelial cells themselves establishing the interface and maintaining the directional absorption of nutrients and secretion of milk.

The present disclosure describes a cell culture apparatus that recapitulates the compartmentalizing capability of the mammary gland that is used to collect milk from mammary epithelial cells grown outside of the body. Such an apparatus can include a scaffold to support the proliferation of mammary cells at the interface between two compartments, such that the epithelial monolayer provides a physical boundary between the nutrient medium and the secreted milk. In addition to providing a surface for growth, the scaffold provides spatial cues that guide the polarization of the cells and ensures the directionality of absorption and secretion. This invention describes the preparation, cultivation, and stimulation of mammary epithelial cells in a compartmentalizing cell culture apparatus for the production and collection of milk for nutritional use (see e.g., FIG. 1).

Preparation of mammary epithelial cells. Mammary epithelial cells are obtained from surgical explants of dissected mammary tissue (e.g., breast, udder, teat), biopsy sample, or raw breastmilk. Generally, after surgical dissection of the mammary tissue, any fatty or stromal tissue is manually removed under aseptic conditions, and the remaining tissue of the mammary gland is enzymatically digested with collagenase and/or hyaluronidase prepared in a chemically defined nutrient media, which should be composed of ingredients that are "generally recognized as safe" (GRAS). The sample is maintained at 37° C. with gentle agitation. After digestion, a suspension of single cells or organoids is collected, either by centrifugation or by pouring the sample through a sterile nylon cell strainer. The cell suspension is then transferred to a tissue culture plate coated with appropriate extracellular matrix components (e.g., collagen, laminin, fibronectin).

Alternatively, explant specimens can be processed into small pieces, for example by mincing with a sterile scalpel. The tissue pieces are plated onto a suitable surface such as a gelatin sponge or a plastic tissue culture plate coated with appropriate extracellular matrix.

The plated cells are maintained at 37° C. in a humidified incubator with an atmosphere of 5% $CO_2$. During incubation, the media is exchanged about every 1 to 3 days and the cells are sub-cultured until a sufficient viable cell number is achieved for subsequent processing, which includes preparation for storage in liquid nitrogen; development of immortalized cell lines through the stable transfection of genes such as SV40, TERT, or other genes associated with senescence; isolation of mammary epithelial, myoepithelial, and stem/progenitor cell types by, for example, fluorescence-activated cell sorting; and/or introduction into a compartmentalizing tissue culture apparatus for the production and collection of milk for human consumption.

Figure 2:
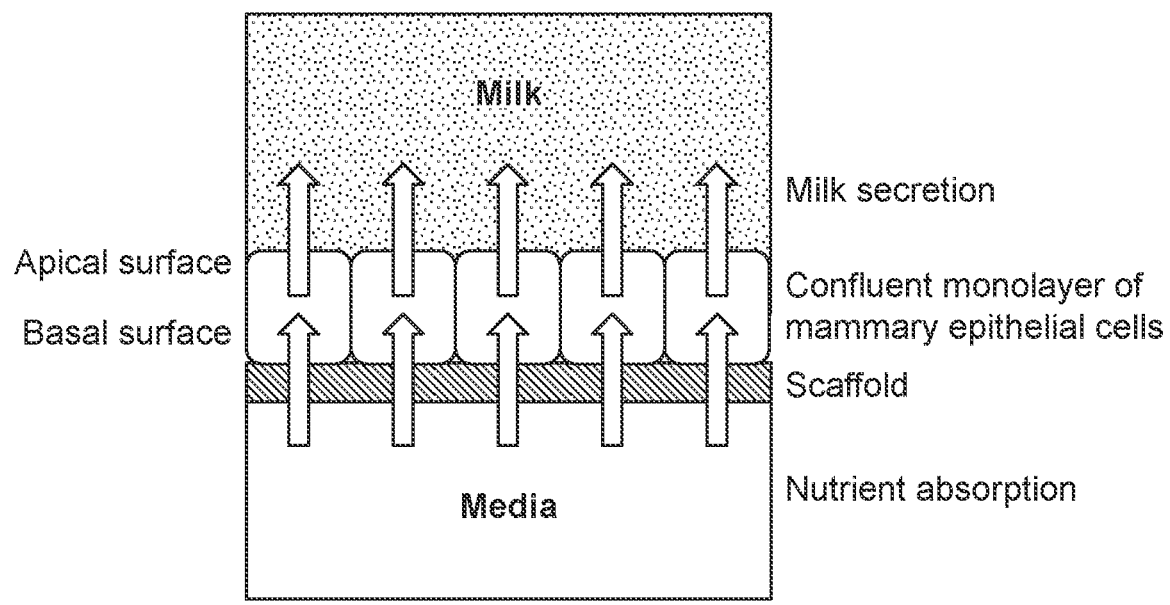
FIG. 2 shows an example of polarized absorption of nutrients and secretion of milk across a confluent monolayer of mammary epithelial cells anchored to a scaffold at the basal surface.

Cultivation of mammary epithelial cells for the production of milk. Milk for nutritional use is produced by mammary epithelial cells isolated as described above and cultured in a format that supports compartmentalized secretion such that separation between the nutrient medium and the product is maintained. The system relies on the ability of mammary epithelial cells to establish a continuous monolayer with appropriate apical-basal polarity when seeded onto an appropriate scaffold positioned at the interface between the apical compartment, into which milk is secreted, and the basal compartment, through which nutrient media is provided (see, e.g., FIG. 2). Transwell® filters placed in tissue culture plates, as well as bioreactors based on hollow fiber or microstructured scaffolds, for example, are used to support these characteristics.

Figure 3:
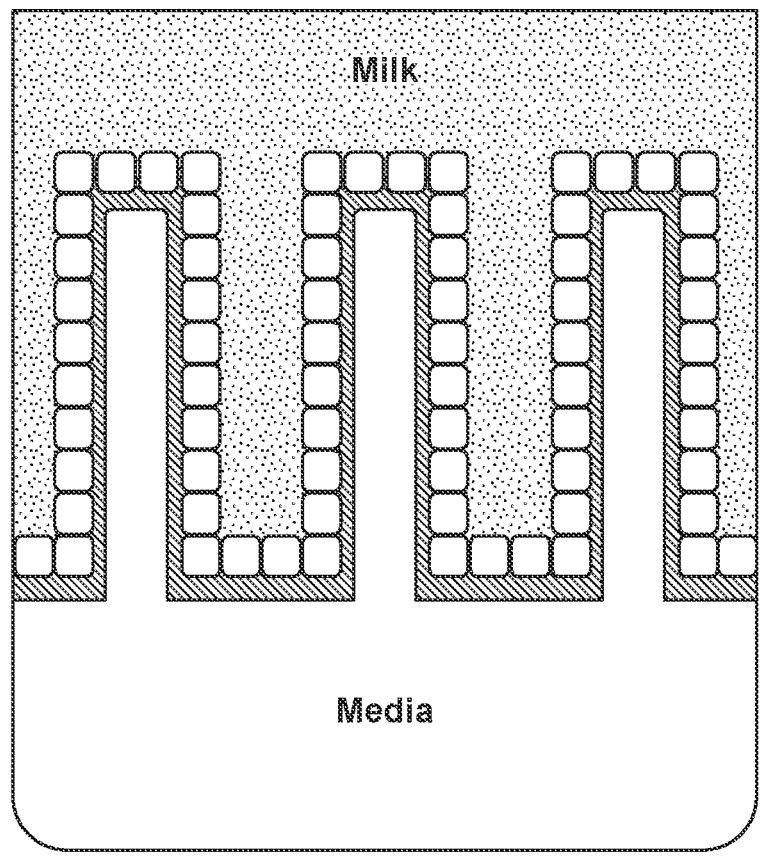
FIG. 3 shows an example micropatterned scaffold that provides increased surface area for the compartmentalized absorption of nutrients and secretion of milk by a confluent monolayer of mammary epithelial cells.
Figure 4:
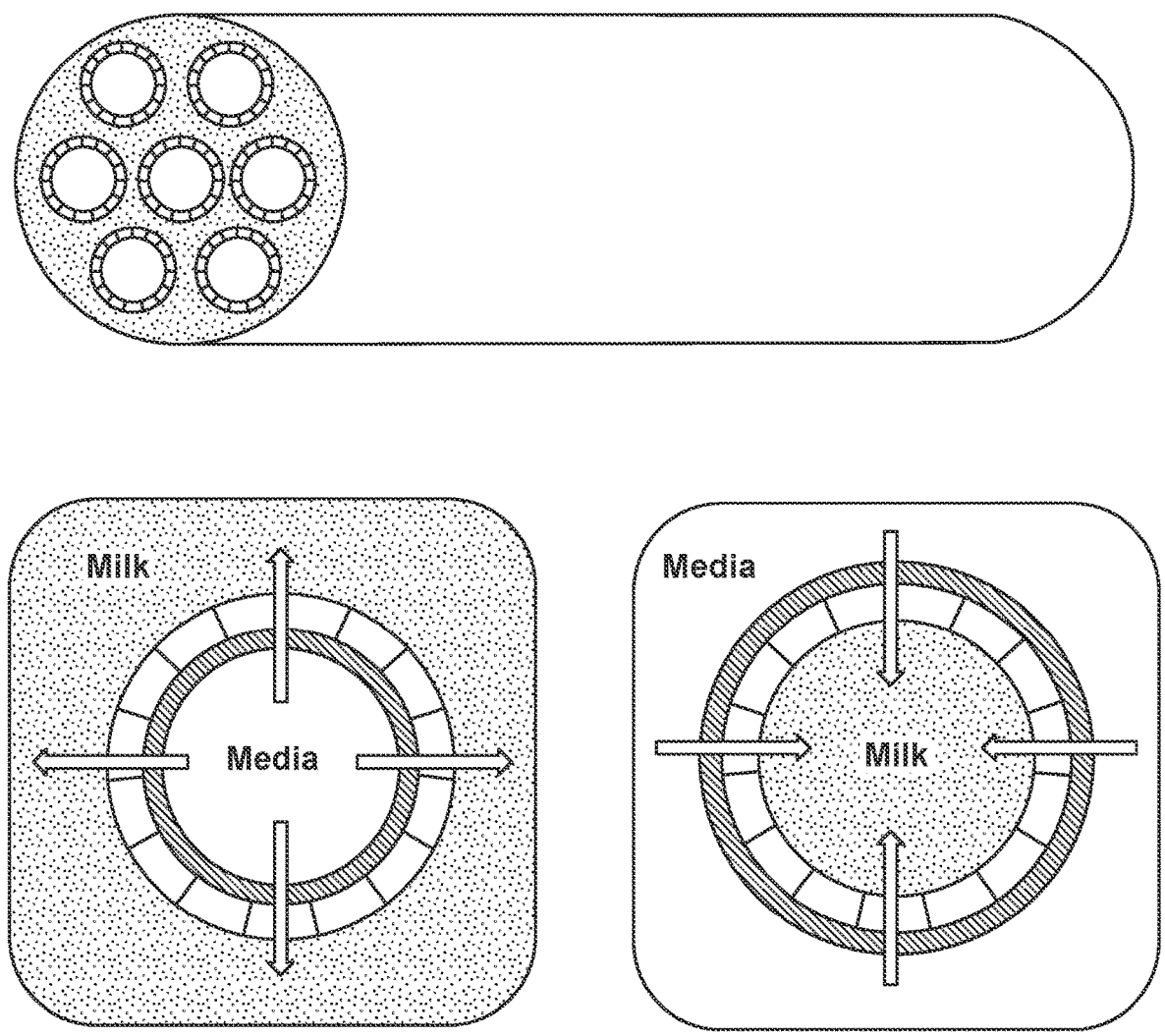
FIG. 4 shows three examples of a hollow fiber bioreactor depicted as a bundle of capillary tubes (top), which can support mammary epithelial cells lining either the external (top and lower left) or internal (lower right) surface of the capillaries, providing directional and compartmentalized absorption of nutrients and secretion of milk.
Figure 5:
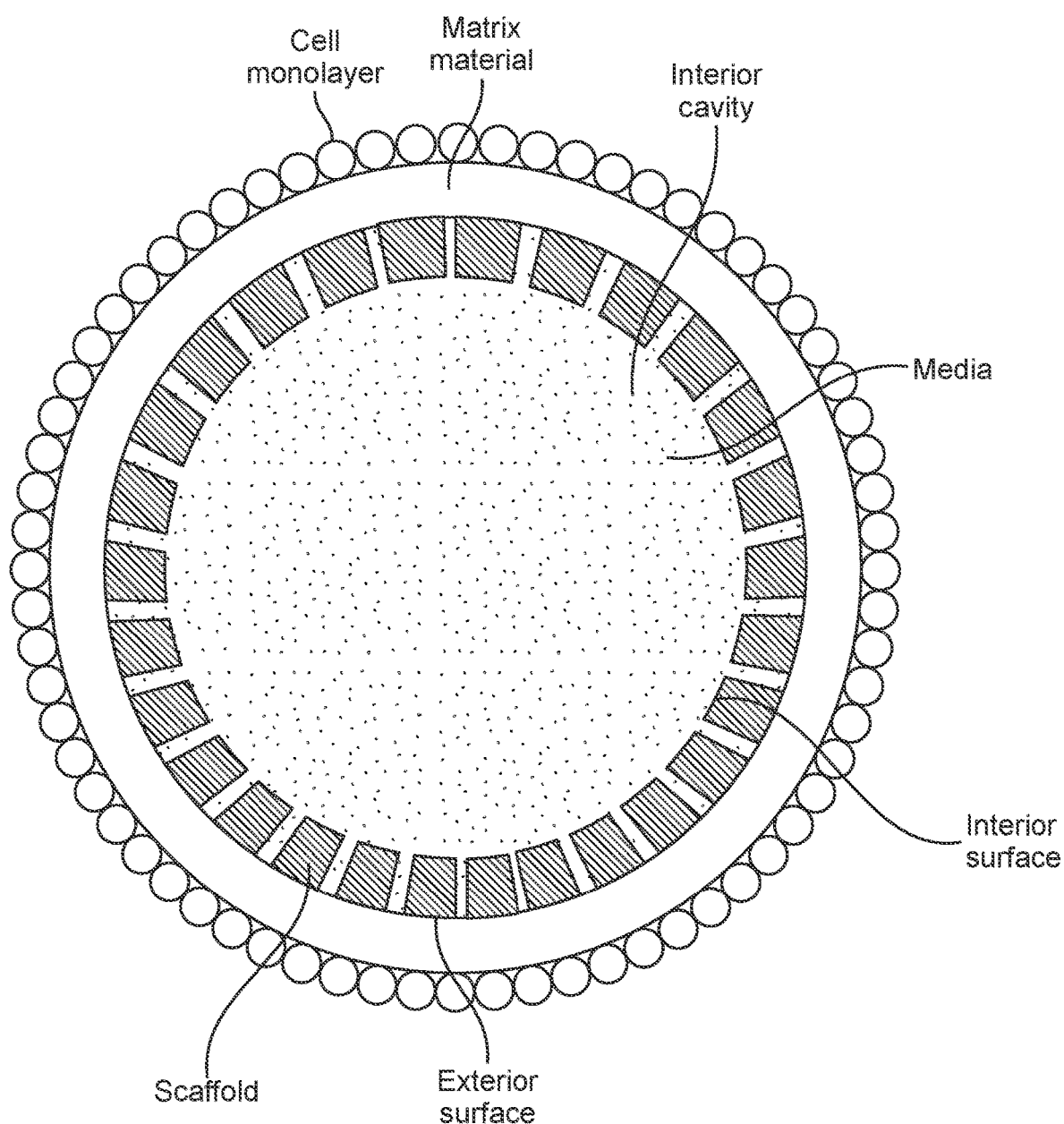
FIG. 5 exemplifies a cross-section of three-dimensional live cell construct. The construct is made up of a scaffold having an interior surface defining an interior cavity/basal chamber and an exterior surface. The interior cavity/basal chamber comprises cell culture media. A matrix material sits on top of the exterior surface of the scaffold. Pores transverse the scaffold from the interior surface to the exterior surface, allowing cell media to contact the basal surface of the cells of the cell monolayer disposed on the matrix material.
Figure 6:
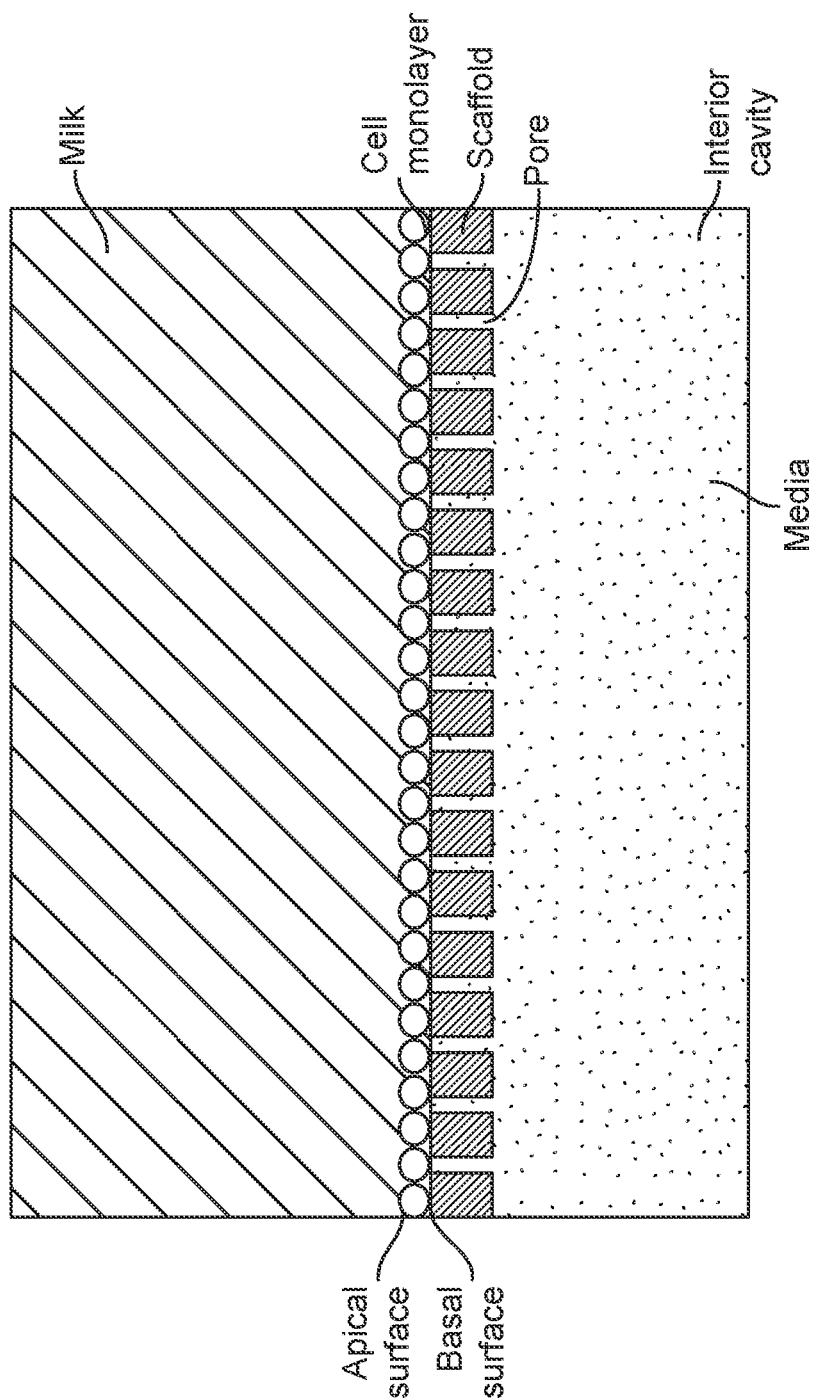
FIG. 6 exemplifies a bioreactor for producing a cultured milk product. The bioreactor is made up of a live cell construct and an apical chamber. The cell construct is made up of a scaffold having an interior surface defining an interior cavity/basal chamber and an exterior surface. The cavity comprises cell culture media. A matrix material sits on top of the exterior surface of the scaffold. Pores transverse the scaffold from the interior surface to the exterior surface, allowing cell media to contact the basal surface of the cells of the cell monolayer disposed on the matrix material. The apical surface of the cells of the cell monolayer secrete the milk/cultured milk product into the apical chamber. The apical chamber and the interior cavity/basal chamber are separated by the cell monolayer.
Figure 7:
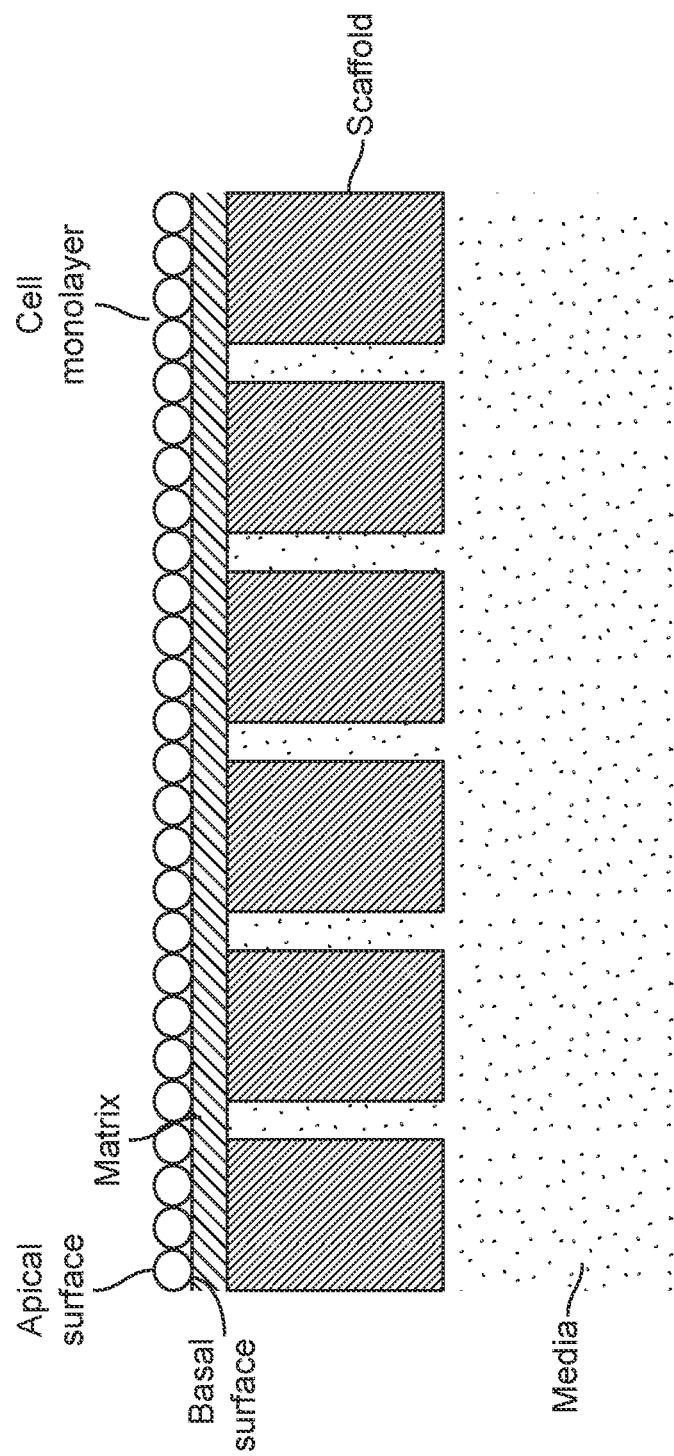
FIG. 7 exemplifies a live cell construct. The construct is made up of a scaffold having an interior surface defining an interior cavity/basal chamber and an exterior surface. The interior cavity/basal chamber comprises cell culture media. A matrix material sits on top of the exterior surface of the scaffold. Pores transverse the scaffold from the interior surface to the exterior surface, allowing cell media to contact the basal surface of the cells of the cell monolayer disposed on the matrix material.

Following the isolation and expansion of mammary epithelial cells, the cells are suspended in a chemically defined nutrient medium composed of food-grade components and inoculated into a culture apparatus that has been pre-coated with a mixture of extracellular matrix proteins, such as collagen, laminin, and/or fibronectin. The cell culture apparatus is any design that allows for the compartmentalized absorption of nutrients and secretion of product from a polarized, confluent, epithelial monolayer. Examples include hollow fiber and microstructured scaffold bioreactors (see, e.g., FIGS. 3 and 4, respectively). Alternatives include other methods of 3-dimensional tissue culture, such as the preparation of decellularized mammary gland as a scaffold, repopulated with stem cells to produce a functional organ in vitro, or collection of milk from the lumen of mammary epithelial cell organoids or "mammospheres" grown either in a hydrogel matrix or in suspension.

The apparatus includes sealed housing that maintains a temperature of about 37° C. in a humidified atmosphere of about 5% $CO_2$. Glucose uptake is monitored to evaluate the growth of the culture as the cells proliferate within the bioreactor. Stabilization of glucose consumption indicates that the cells have reached a confluent, contact-inhibited state. The integrity of the monolayer is ensured using transepithelial electrical resistance. Sensors monitor concentrations of dissolved $O_2$ and $CO_2$ in the media at multiple locations. A computerized pump circulates media through the bioreactor at a rate that balances the delivery of nutrients with the removal of metabolic waste such as ammonia and lactate. Media can be recycled through the system after removal of waste using Lactate Supplementation and Adaptation technology (Freund et al. 2018 *Int J Mol Sci.* 19(2)) or by passing through a chamber of packed zeolite.

Stimulation of milk production. In vivo and in cultured mammary epithelial cells, the production and secretion of milk is stimulated by prolactin. In culture, prolactin can be supplied exogenously in the nutrient media at concentrations approximating those observed in the body during lactation, e.g., about 20 ng/mL to about 200 ng/mL. Purified prolactin can be obtained commercially; however, alternative methods of providing prolactin or stimulating lactation are employed, including expression and purification of the recombinant protein from microbial or mammalian cell cultures. Alternatively, conditioned media prepared by culturing cells that express and secrete prolactin can be applied to mammary epithelial cell cultures to stimulate lactation. Bioreactors can be set up in series such that media passing through a culture of cells expressing prolactin or other key media supplements is conditioned prior to exposure to mammary cells grown in a compartmentalizing culture apparatus as described.

Other approaches to upregulate milk production and/or spare the use of exogenous prolactin include molecular manipulation of the signaling pathways that are regulated by binding of prolactin to its receptor on the surface of mammary epithelial cells, such as the following: (a) expression of constructs targeting the posttranslational modification of prolactin; (b) expression of alternative isotypes of the prolactin receptor; (c) expression of a chimeric prolactin receptor in which the extracellular domain is exchanged with the binding site for a different ligand; (d) introduction of a gene encoding a constitutively or conditionally active prolactin receptor or modified versions of its downstream effectors such as STAT5 or Akt; (e) knockout or modification of the PER2 circadian gene; and/or (f) molecular approaches aimed at increasing the rate of nutrient uptake at the basal surface of the mammary epithelial monolayer.

Collection of milk. Secreted milk is collected continuously or at intervals through, for example, a port installed in the apical compartment of the culture apparatus. A vacuum is applied to the port to facilitate collection and also contributes to the stimulation of further production. The collected milk is packaged into sterile containers and sealed for distribution, frozen or lyophilized for storage, or processed for the extraction of specific components.

The present invention provides mammary epithelial cell cultures for the production of milk for nutritional use. In addition to human breast milk, this method may be used to produce milk from other mammalian species, for example, for human consumption or veterinary use. Because it has not been previously possible to produce milk outside the body, this technology may result in novel commercial opportunities, in addition to providing an alternative mode of production for existing products. The social and economic effects of the commercial development of this technology are broad and far reaching. Production of human breast milk from cultured cells may provide a means to address infant malnutrition in food-scarce communities, provide essential nutrients to premature infants who are unable to breastfeed, and offer mothers a new option for feeding their babies that provides optimal nutrition with the convenience of infant formula. Production of cow or goat milk provides an opportunity to reduce the environmental, social, and animal welfare effects of animal agriculture. The process described here addresses an important gap in the emerging field of cellular agriculture and introduces an opportunity to dramatically update the human food supply without compromising our biological and cultural attachment to the most fundamental of our nutrition sources.

The foregoing examples are illustrative of the present invention, and are not to be construed as limiting thereof. Although the invention has been described in detail with reference to preferred embodiments, variations and modifications exist within the scope and spirit of the invention as described and defined in the following claims.

What is claimed is:

1. A method of producing an isolated milk product from cultured mammary cells, the method comprising:
   (a) culturing a live cell construct in a bioreactor under conditions which produce the milk product,
   said live cell construct comprising:
      (i) a three-dimensional scaffold having an exterior surface, an interior surface defining an interior cavity, and a plurality of pores extending from the interior surface to the exterior surface;
      (ii) a matrix material disposed on the exterior surface of the three-dimensional scaffold;
      (iii) a culture medium disposed within the interior cavity and in fluidic contact with the internal surface; and
      (iv) a confluent monolayer of polarized mammary cells disposed on the matrix material, wherein the mammary cells are selected from the group consisting of: live primary mammary epithelial cells, live mammary myoepithelial cells, live immortalized mammary epithelial cells, and live immortalized mammary myoepithelial cells, and wherein the polarized mammary cells comprise an apical surface from which the cultured milk product is secreted and a basal surface;
   said bioreactor comprising an apical compartment that is in fluidic contact with the apical surface of the mammary cells, is substantially isolated from the interior cavity of the live cell construct, and is substantially free of cell culture medium; and
   (b) isolating the cultured milk product secreted into the apical compartment from the apical surface of the mammary cells.

2. The method of claim 1, wherein the basal surface of the mammary cells is in fluidic contact with the culture medium.

3. The method of claim 1, wherein total cell density of mammary cells within the bioreactor is at least $10^{11}$.

4. The method of claim 1, wherein total surface area of mammary cells within the bioreactor is at least 1.5 m$^2$.

5. The method of claim 1, wherein the matrix material comprises one or more extracellular matrix proteins.

6. The method of claim 1, wherein the culturing is carried out at a temperature of about 27° C. to about 39° C.

7. The method of claim 1, wherein the culturing is carried out at an atmospheric concentration of $CO_2$ of about 4% to about 6%.

* * * * *